US005838446A

United States Patent [19]
Meth et al.

[11] Patent Number: 5,838,446
[45] Date of Patent: Nov. 17, 1998

[54] DETERMINATION OF COATING ADHESION

[75] Inventors: Jeffrey Scott Meth, Newark; Stephen John Bennison, Wilmington, both of Del.

[73] Assignee: E. I. du Pont de Nemours and Company, Wilmington, Del.

[21] Appl. No.: 857,838

[22] Filed: May 16, 1997

Related U.S. Application Data

[60] Provisional application Nos. 60/017,148, May 17, 1996 and 60/031,103, Nov. 26, 1996.
[51] Int. Cl.$^6$ ........................................................ G01L 1/24
[52] U.S. Cl. .............................................. 356/372; 73/588
[58] Field of Search ..................................... 356/371, 372, 356/446; 73/582, 588

[56] References Cited

U.S. PATENT DOCUMENTS

| 4,972,720 | 11/1990 | Wu ............................................. 73/801 |
| 5,438,402 | 8/1995 | Gupta ...................................... 356/353 |

OTHER PUBLICATIONS

Lambourne, R., *Paint and Surface Coatings: Theory and Practice*, Ellis Horwood, Ltd., West Sussex, England, 677, 1987.
Anderson, G. P. et al., *Analysis and Testing of Adhesive Bonds*, Academic Press, New York, 24–29, 1977.
Dannenberg, H., "Measurement of Adhesion by a Blister Method," *J. Appl. Polym. Sci.*, 5(14), 125–134, 1961.
Timoshenko, S. P. et al., *Theory of Elasticity*, McGraw–Hill, New York, 244–247, 1970.
Siegman, A. E., *Lasers*, University Science Books, Mill Valley, CA, 587, 782–783, 1986.
Timoshenko, S. et al., *Theory of Plates and Shells*, McGraw–Hill, New York, 54–57 and 72–75, 1959.
Ferry, J. D., *Viscoelastic Properties of Polymers*, John Wiley & Sons, New York, 280–290, 1980.

Bennett, S. J. et al., "Adhesive fracture mechanics," *Int. J. of Fracture*, 10(1), 33–43, 1974.
Sneddon, I. N. et al., *Crack Problems in the Classical Theory of Elasticity*, John Wiley & Sons, Inc., New York, 130–135, 138–139, 1969.
Andrews, E. H. et al., "Fracture energy of epoxy resin under plane strain conditions," *J. of Materials Science*, 13, 1680–1688, 1978.
Valli, J., "A review of adhesion test methods for thin hard coatings," *J. Vac. Sci. Technol.*, A 4(6), 3007–3013, 1986.
Lee, W–C et al., *Metallized Plastics 2*, ed. By K. L. Mittal, Plenum Press, New York, 449–460, 1991.
Vossen, J. L., "Measurements of Film–Substrate Bond Strength by Laser Spallation," Adhesion Measurement of Thin Films, Thick Films, and Bulk Coatings, *ASTM Spce. Tech. Publ. 640*, 122–133, 1978.
Farris, T. N. et al., "Williams' blister test analyzed as an interface crack problem," *Int. J. of Fracture*, 27, 91–103, 1985.

(List continued on next page.)

*Primary Examiner*—Richard A. Rosenberger

[57] ABSTRACT

An infrared laser is used to irradiate a sample, which preferably comprises a substrate, onto which an opaque basecoat is applied, which basecoat in turn is coated with a clearcoat. The laser pulse photoablates the basecoat at an interface between the basecoat and the clearcoat, and a blister forms in the clearcoat due to an increase in pressure from the ablation. The irradiation can be done a number of times on fresh areas of the sample and with increased laser energy. A critical energy value is determined which is the energy where a crack begins to propagate from the blister formed. Another laser is used to measure the amount of light reflected off the top surface of the blister which passes through the middle of an aperture. These values, along with others such as the size of the blister and the modulus of the clearcoat, are used to determine the adhesion strength at the interface of the basecoat and clearcoat.

14 Claims, 12 Drawing Sheets

OTHER PUBLICATIONS

Allen, M. G. et al., "Analysis of Critical Debonding Pressures of Stressed Thin Films in the Blister Test," *J. Adhesion*, 25, 303–315, 1988.

Chang, Y. et al., "The Constrained Blister—A Nearly Constant Strain Energy Release Rate Test for Adhesives," *J. Adhesion*, 27, 197–211, 1989.

Williams, M. L., "The Continuum Interpretation for Fracture and Adhesion," *J. of Appl. Polym. Sci.*, 13, 29–40, 1969.

Williams, M. L., "The Fracture Threshold for an Adhesive Interlayer," *J. of Appl. Polym. Sci.*, 14, 1121–1126, 1970.

Williams, M. L., "The Relation of Continuum Mechanics to Adhesive Fracture," *J. Adhesion*, 4, 307–332, 1972.

DETERMINATION OF COATING ADHESION

This application claims the priority benefit of U.S. Provisional Application 60/017,148, filed May 17, 1996 and U.S. Provisional Application 60/031,103, filed Nov. 26, 1996.

FIELD OF THE INVENTION

This invention relates to a method for measuring the adhesion between two coatings applied to a substrate or between a coating and a substrate whereby laser induced debonding is coupled with spectroscopic analysis of a blister formed in the coating and related to an adhesion parameter.

TECHNICAL BACKGROUND

It is well recognized by those skilled in the art that the adhesion of a coating to a substrate is key to its performance. Measurement and quantification of adhesion has been difficult and is often dependent on the coating and substrate being tested. There are many ways to measure the adhesion parameter, G, which has units of $J/m^2$, which is characteristic of a film system, and the type of measurement selected depends on the particular system under study. For polymeric coatings, techniques in common usage are the cross-hatch/peel test, the X hatch test (ASTM Designation: D-3359-93) and the blister test. In the cross-hatch/peel test, a coated sample plate is scribed in orthogonal directions, tape is applied to the coating surface and the tape is then removed. The adhesive strength is related to how much of the coating is removed with the tape. In the X hatch test, a coated sample plate is scribed with an X, tape is applied to the coating surface, and the tape is then removed. The cross-hatch/peel test and the X hatch test are highly qualitative and suffer from the drawback of variability in the speed and angle at which the tape is removed. The cross-hatch/peel test is also inadequate when G is large because the adhesion of the tape to the coating surface to be peeled is sometimes less than the adhesion of the test coating surface to the substrate. In addition, the cross-hatch/peel test shows failure at the weakest interface of the system, which is not necessarily the desired interface. (See generally R. Lambourne, ed., *Paint and Surface Coatings: Theory and Practice*, Ellis Horwood, Ltd., West Sussex, England, 1987, p. 677, and G. P. Anderson, et al., *Analysis and Testing of Adhesive Bonds*, Academic Press, New York, 1977.)

In the blister test, a coating is bonded to a substrate except for a central portion with a defined radius. A fluid or a gas is introduced between the substrate and the coating at this central portion. As the pressure is increased, the radius remains constant until a critical pressure is reached, whereupon the blister's radius increases, indicating adhesive failure at the interface. There are drawbacks associated with the blister test. The most prominent problem is that the sample must undergo special preparation to create the necessary geometry for testing, such as holes drilled through the substrate and initial debonded areas formed. Large G values call for large blister pressures, requiring that the testing device be a high-pressure vessel. In addition, the rate of fracture must be controlled. (See generally H. Dannenberg, *J. Appl. Polym. Sci.*, 5(14), pp. 125–134, 1961.)

There are currently no suitable objective test methods to quantify adhesion between component films in multilayer paint structures. A quantitative method would aid development of new paint formulations and allow assessment of paint performance under conditions which can cause interlayer decohesion and fracture. The current invention addresses this deficiency by presenting a new method for the quantitative determination of adhesion between polymer films.

It is an object of the present invention to provide a method which can quantitatively and reproducibly measure the adhesion parameter, G, and thus, the adhesion of a coating, which method does not require special sample preparation, has a controlled rate of fracture, and can be used on systems with weak or strong bonding.

SUMMARY OF THE INVENTION

The present invention comprises a process for determining the adhesion of a film system, comprising the steps of: (a) applying a pulse of electromagnetic radiation to a film system, said pulse having sufficient intensity to ablate a portion of the film system under adiabatic conditions; (b) forming a blister in the film system with the electromagnetic radiation; (c) determining a critical pulse energy occurring when the blister is strained to the point where an interfacial crack just begins to form; (d) determining an initial curvature of the blister formed at the critical pulse energy; (e) determining a critical internal pressure of the blister at the critical pulse energy; and (f) relating the critical internal pressure of the blister to an adhesion parameter to determine the adhesion of the film system.

DETAILS OF THE INVENTION

Figure 1:
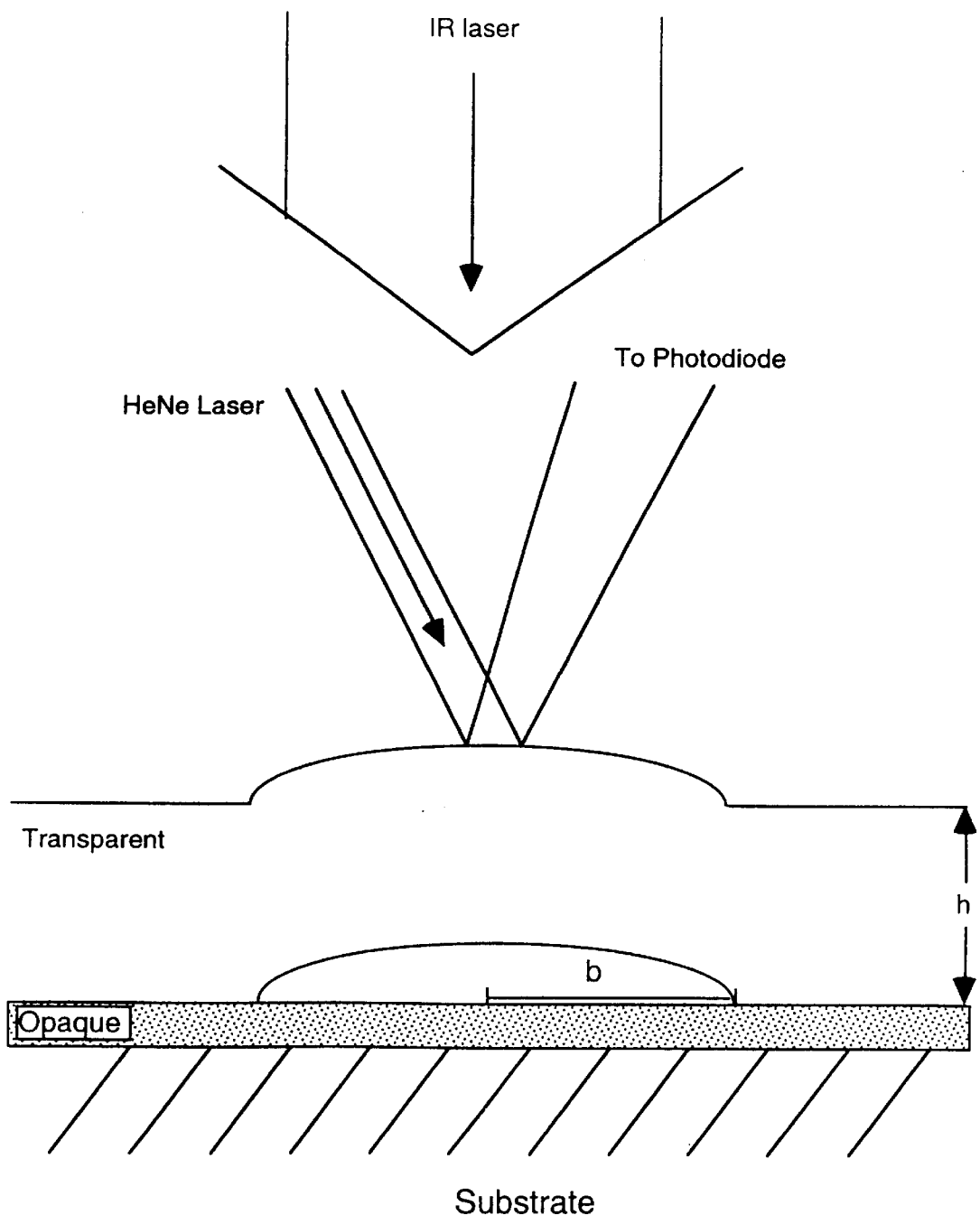
FIG. 1 is a schematic representation of an embodiment of the present invention wherein a pulsed infrared (IR) laser ablates the surface of an opaque material coated on a substrate, producing a blister of radius, b, in a transparent coating of thickness, h. A Helium-Neon (HeNe) laser beam reflects off the surface of the blister to a photodiode which is used to detect the curvature of the blister.

The present invention is used to determine the adhesion of a film system by calculating an adhesion parameter, $G(J/m^2)$, the work of adhesion. By "adhesion" is meant a state of intimate contact between two dissimilar materials of n-dimension separated by a boundary of n-1 dimension which corresponds to a physically realizable boundary or interface. Likewise, "deadhesion" is the loss of adhesion, denoting the separation of the two dissimilar materials at the interface. Similarly, "decohesion" is the loss of cohesion denoting the separation within either of the materials that comprise the interface.

The term "film system" is used herein to describe a combination of materials that are considered finite in one dimension (the thickness dimension) and infinite in the other two dimensions when one is considering interfacial properties. In the process of the present invention, a film system can comprise a substrate, and at least one transparent coat. The film system can further comprise at least one opaque coat applied to the top surface of the substrate. The transparent coat is applied to a top surface of the substrate, or alternatively, if present, to a top surface of the last applied at least one opaque coat. Preferably, the opaque coat and transparent coat comprise organic polymers. By "coat" or "coating" is meant a film or thin layer applied to the substrate or to a previously applied coating. The coating can be applied by methods including spraying, rushing, rolling, vapor deposition, vacuum and the like. For example, a film system in an automotive paint application can comprise a metal substrate, an electrocoat, a primer, a basecoat and a topcoat. Electrocoats, primers and basecoats are generally opaque however unpigmented embodiments of these coats can render them transparent. Topcoats are generally clear or tinted. Both clear and tinted coatings are considered to be transparent herein. Representative examples of a film system are an electrocoat applied to a metal substrate with a transparent primer applied to a top surface of the electrocoat; an opaque primer applied to a substrate and an unpigmented basecoat applied to a top surface of the primer; a clear topcoat applied to an opaque substrate, and an opaque basecoat applied to a substrate with a clear topcoat applied to a top surface of the basecoat.

By "substrate" is meant any solid, rigid surface on which a coating can be applied. As used herein, the substrates are generally opaque, although a transparent substrate can be used provided the film system comprises an opaque coat applied to the top surface of the substrate. Representative examples of substrates are bare or primed metals, such as stainless steel, phosphated cold-rolled steel, aluminum, and copper; polymers, such as thermoplastic olefin; and ceramics, such as silicon.

A coating or a substrate is considered transparent herein if the 1/e (e being the natural logarithm) intensity absorption depth of the coating is greater than the coating thickness. A coating is considered opaque if the 1/e intensity absorption depth is less than about 5 microns.

In the process of the present invention, a pulse of electromagnetic radiation is applied to the film system in a small, localized region. No one position on the sample is ever exposed to more than a single pulse for data acquisition. A laser beam can be used and focused down with a lens to confine the pulse in the lateral dimension. To confine the pulse in the propagation direction, it is necessary to have a relatively sharp interface within the film system between a medium in which the pulse propagates with little loss of intensity, for example a clear or tinted topcoat, and a medium in which the light will not propagate at all, for example an opaque basecoat.

The pulse must have sufficient intensity to ablate a portion of the film system, namely the top surface of an opaque coating which is in contact with a transparent coating or the top surface of an opaque substrate in contact with a transparent coating. A pulse applied for about 10 to about 10,000 picoseconds is sufficient to ablate a portion of most film systems. The pulse is applied under adiabatic conditions. By "adiabatic conditions" is meant the process occurs rapidly enough that thermal diffusion does not occur to any significant extent. Thermal diffusion can cause the physical properties of any polymer used in the film system to change, for example modulus and Poisson's ratio, and these changes can affect later steps in the present process.

The pulse of electromagnetic radiation can be produced by a laser, such as an IR laser. In the examples described herein, the laser used was a CW-modelocked Nd:YLF (CW=continuous wave, YLF=Yttrium Lithium Fluoride, $LiYF_4$) laser (Quantronix Corp., New York), which includes a regenerative oscillator/amplifier (Continuum, Santa Clara, Calif.). This IR laser produces pulses with a wavelength of about 1.053 microns, having about a 50 picosecond pulse duration, and having an energy variable up to 1 mJ.

As a result of the electromagnetic radiation, a blister forms in the film system. For example, in a film system comprising an opaque basecoat applied to a top surface of the substrate and a transparent topcoat applied to the top surface of the basecoat, small pieces of the basecoat are liberated upon ablation resulting in a recoil momentum directed away from the surface of the opaque coating which force pushes up on the bottom surface of the transparent topcoat. As shown in FIG. 1, an IR laser is applied to a film system wherein an opaque basecoat is ablated, and a pressure is generated on the underside of the transparent topcoat producing a blister at the interface between the two coats. The presence of the rigid substrate prevents significant deformation of the opaque basecoat. The internal pressure of the blister deforms the transparent topcoat causing decohesion or deadhesion of the transparent topcoat from the opaque basecoat whereby the blister forms directly above the ablated area.

Ablation destroys the mechanical integrity of the opaque basecoat near its top surface. Left behind in the opaque basecoat is a crater, generally circular in shape with a depth relatively uniform across its surface. The depth and radius of the crater are dependent upon the intensity of the pulse and the pigmentation and chemical composition of the opaque film. For a pulse with an energy of about 100 microjoules, and a duration of about 50 picoseconds, the crater is generally a few microns deep, and the radius is generally about 20 $\mu$m to about 100 $\mu$m, preferably about 50 $\mu$m.

In the process of the present invention, a critical pulse energy is determined which occurs when the blister is strained to the point where an interfacial crack just begins to form. In order to determine this critical pulse energy, ablation can be repeated on different areas of the sample using increasing pulse energy. As the pulse energy is increased, more ablation occurs, the internal pressure of the resulting blister increases, and consequently the strain energy in the blister increases. "Strain energy" is defined as "the work done on an element and stored within it" (see S. P. Timonshenko, et al., *Theory of Elasticity*, McGraw-Hill, New York, 1970, p. 244. ) At the critical pulse energy, the total energy of the system is less when energy is expended to create new surfaces in the system through crack propagation, versus when that energy is expended by increasing the energy stored as elastic strain energy. At the critical pulse energy, the blister expands radially into the region of the sample that was not ablated, producing an annular debond area, as opposed to expanding vertically, raising the height of the blister while keeping its radius constant. At this critical pulse energy, the Griffith criterion for crack propagation is exceeded. The "Griffith criteria for crack propagation", is discussed in G. P. Anderson, et al., *Analysis of Testing of Adhesive Bonds*, Academic Press, New York, 1977, p. 27, and occurs when "the cohesive fracture commences at a critical applied stress, and when the incremental loss of strain energy of deformation with increasing fracture area just equals the work required to create a new fracture surface." Thus, at the critical pulse energy, a crack propagates radially when the decrease in strain energy with increasing crack area is balanced by the increased surface energy of the newly formed surfaces in the debond area. For different film systems, there are different blister radii at the critical pulse energy.

The critical pulse energy can be determined by exposing the film system sample to a range of pulse energies varied from a threshold energy value where a blister is just detectable to an energy value above that where decohesion begins, i.e., above the energy value where the debond (crack) starts to propagate radially. Inspection of the blisters to determine when decohesion occurs can be done with a microscope. It may be necessary to repeat blister formation at various energies a number of times in order to pinpoint the critical pulse energy.

At the critical pulse energy, a critical internal pressure exists within the blister. Although the internal pressure of the blister at the critical pulse energy cannot be measured directly, it can be determined by relating various other parameters of the film system, as measured at the critical pulse energy. These parameters comprise: the initial radius of curvature of the blister, $R_c$; the thickness of the transparent coat, h; the transparent coat modulus, E; the radius of the blister, b; and Poisson's ratio of the transparent coat, $\upsilon$.

In the process of the present invention, the initial curvature of the blister at the critical pulse energy is determined. The initial radius of curvature of the blister formed at each pulse energy is measured about 1–20 microseconds after the blister has been created by the laser pulse. The initial radius of curvature of each of these blisters can be measured by reflecting a low power, continuous wave laser beam, such as from an HeNe laser, from the top surface of the blister and measuring the beam spot size, w, with an aperture. As used herein, the aperture is a piece of material that is opaque that has a circular hole cut in the middle of it. For example, a washer with a known internal diameter can be simply taped to a 2 inch square plastic holder and serve as an aperture.

The initial curvature of the blister (which is the inverse of the initial radius of curvature) is a linear function of the pulse energy. By constructing a plot of the initial curvature versus the pulse energy, a plot can be made to a straight line. From the straight line fit, the measured values of the initial curvature can be extrapolated to calculate the initial curvature of the blister at a value of the pulse energy equal to the critical pulse energy.

Figure 2:
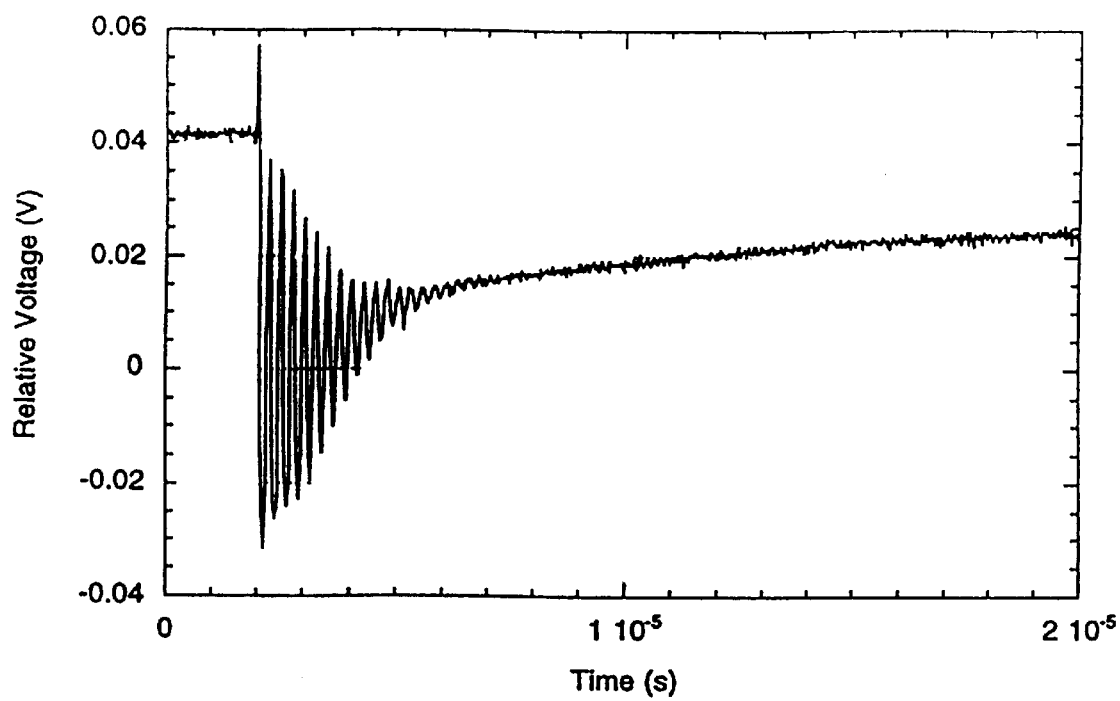
FIG. 2 is a typical oscilloscope trace of HeNe intensity observed during the present process.

In FIG. 2 a digitizing oscilloscope trace is displayed. Before the laser pulse has impinged upon the sample, a fixed amount of light from the HeNe beam is transmitted through the aperture and is recorded by a photodiode. That level of the signal is the horizontal line that exists for the first 2 microseconds in FIG. 2. When the IR laser pulse interacts with the sample, the blister forms. The HeNe beam diverges because it is being reflected from a convex surface. Some of the light is no longer transmitted through the aperture because it is blocked. The amount of light transmitted by the aperture has decreased. This causes the response of the photodiode to decrease, so the trace of the oscilloscope goes down. Equations 1 and 2 enable one to relate the voltage on the y axis of FIG. 2 to the spot size of the HeNe beam, and then to the radius of curvature of the blister. As can be seen in FIG. 2, the curvature is not constant in time. Thus, it must be averaged. This is accomplished by averaging the photodiode voltage over time from 2–5 microseconds on the trace shown in FIG. 2. This is generally the time window that was averaged in the examples herein, but some are variable. At longer times (greater than about 5 microseconds) in FIG. 2, the photodiode signal can be seen to be recovering. This is due to the relaxation of the blister over time, as the internal blister pressure decreases. To get an accurate measurement of the internal pressure, the blister curvature in the initial moments must be measured, before relaxation occurs. This is identified as the initial radius of curvature of the blister.

The beam spot size of the laser is related to the amount of light passing through the aperture. The convexity of the surface of the blister causes the HeNe beam to diverge. When the laser beam reflects off the curved surface, its beam parameters are changed in a known way. Thus, the beam spot size can be measured and the curvature of the blister at the surface can be deduced using Gaussian beam propagation theory (see Lasers by A. E. Siegman, University Science Books; Mill Valley, Calif. 1986). From its origin, the HeNe laser travels a distance, $d_0$, to a lens of focal length, f. The beam is then focused through a distance $d_2$ onto the blister's surface with a radius of curvature $R_c$, whereupon it is reflected and travels a distance $d_4$ to an aperture. By measuring the transmitted intensity through the aperture, the beam spot size can be determined. The measured spot size, w, is related to the beam propagation parameter by Equation (1) below:

$$w = \sqrt{-\frac{\lambda}{\pi Im\left(\frac{1}{q_s}\right)}} \qquad \text{Equation (1)}$$

wherein:

$$q_5 = \frac{\left( (-d_o - q_0 + f) + \frac{2}{R_c} \ ((-d_o - q_o + f)d_2 + f(d_o + q_o)) \right) d_4 + ((-d_o - q_o + f)d_2 + f(d_o + q_o))}{(-d_o - q_o + f) + \frac{2}{R_c} \ ((-d_o - q_o + f)d_2 + f(d_o + q_o))}$$

Equation (2);

$\lambda$ is the wavelength of the laser beam;

Im denotes the operation of taking the imaginary component;

$w_0$ is the initial beam spot size (which is dependent on the type of laser used); and $q_0 = \iota \pi w_0^2 / \lambda$ ($q_0$ is not to be confused with the internal blister pressure, and $\iota$ is square root of $-1$).

Therefore, by measuring the spot size, the propagation distances, and the focal length of the lens, Equation (2) can be solved and substituted into Equation (1), then Equation (1) can be inverted to obtain $R_c$ in terms of w.

From a computer within the digitizing oscilloscope data can be transferred from the scope to another computer using one of the commercially available programs such as Visual Basic from Microsoft or Lab Windows from National Instruments. Curvature values can be tabled from the trace by using a program that calculates laser beam spot size from the intensity transmitted through a circular aperture, then uses Equation 2 to calculate curvature from spot size. Curvature values can be tabulated using Kaleidagraph (Synergy Software, Reading, Pa.). Kaleidagraph can also be used to plot lines and fit them to the data points, such as for FIG. 3. Included herein is source code based on VisualBasic for transferring data from the scope to the computer (see "getdata1" routine) and for calculating the curvature of the blister (see "analyze1" routine).

Figure 3:
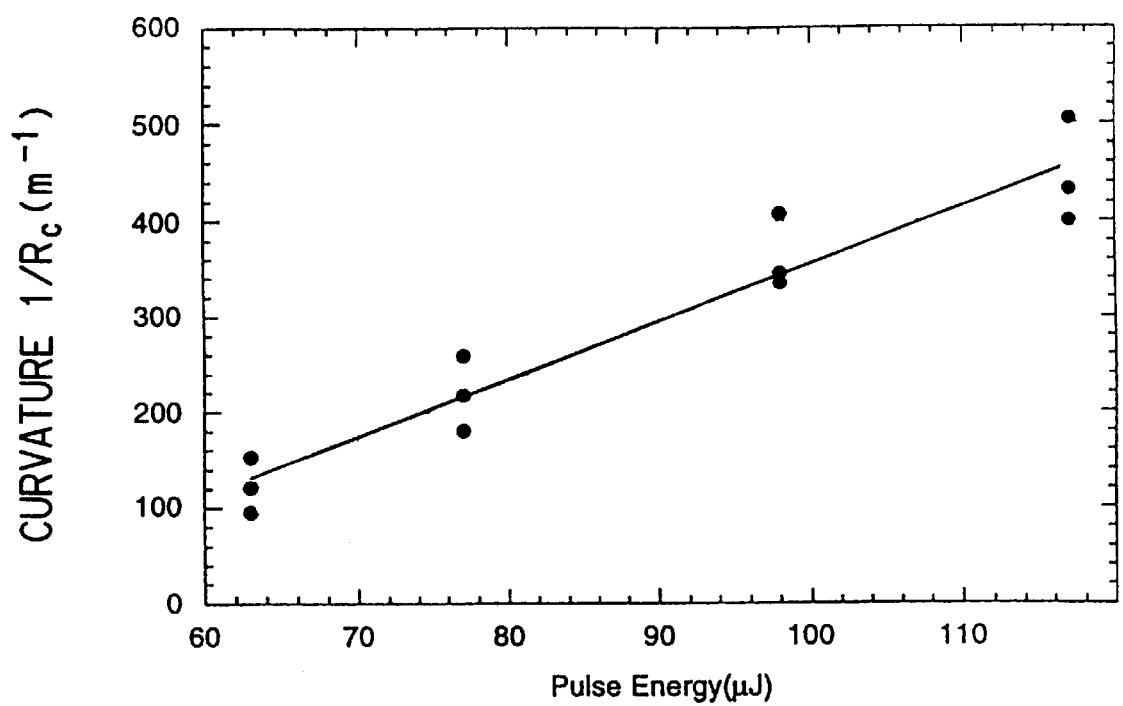
FIG. 3 is a plot of initial curvature of a blister versus pulse energy using the data of Example 42, demonstrating linear dependence (y=−250.21+6.055x, R=0.96054 wherein R is the Pearson sample correlative coefficient).

In FIG. 3, the initial curvature of the blister as a function of pulse energy is shown. The initial curvature is the inverse of the initial radius of curvature of the blister. This curvature is derived by applying Equations 1 and 2 to an oscilloscope trace such as the one shown in FIG. 2 and explained above. Three blisters are demonstrated for each pulse energy to exemplify shot-to-shot reproducibility. There is clearly a linear dependence of the curvature on the pulse energy. The critical pulse energy, that is, the pulse energy at which a crack just begins to initiate, for Example 42 herein, is 117 microjoules (see Table 3, row 42, column 1), corresponding to the highest energy at which data is displayed in FIG. 3. The data is fit to a straight line, and the least squares fitting parameters, along with the Pearson sample correlation coefficient "R" value of the fit, are displayed in FIG. 3. The least squares parameters are also collected in the Table 3 where column 2 shows the slope and column 3 shows the intercept. Next, the value of 117 is substituted for "x" in the least squared fit to obtain the initial curvature of the blister at the critical pulse energy. For Example 42, the initial curvature of the blister at the critical pulse energy is 458 inverse meters (See Table 3, row 42, column 4). This figure demonstrates that, to obtain the value of the adhesion parameter for the example, twelve separate blisters were created. The initial curvature of the blister is then related to the critical internal blister pressure as detailed below.

Links to relate the initial curvature of the blister to the critical internal pressure of the blister and the critical internal pressure to the work of adhesion can be established by solving the mechanical problem of the deformation of a thick plate or disk which has been subjected to an axisymmetric, uniform pressure.

Mechanical deformation in a film system can be solved, for example, by using Love's equation, S. P. Timoshenko and J. N. Goodier, *Theory of Elasticity*, McGraw Hill, New York, 1970, and provides information pertaining to the stresses, strains, displacements and strain energy of the blister. This information can then be used to relate the initial curvature at the critical pulse energy of the blister to the internal pressure of the blister at the critical pulse energy, and to relate the internal pressure to the adhesion parameter. In addition, it provides the basis for Equations 3 and 6.

An implicit assumption made herein is that the ablation process acts like a uniform pressure on the underside of the transparent coat. Thus, a method of stress potential functions can be used to determine the stresses, strains and strain energy for various boundary conditions of the transparent coat of the film system. The stress potential function can be expanded in a series, then physical boundary conditions used to determine the multiplicative constants for each term in the series.

Four different sets of boundary conditions are presented herein and are labeled as cases 1–4. These boundary conditions are representative of the entire range of possible boundary conditions that could conceivably be used to model the mechanical deformation of the blister. The problem is solved herein using cylindrical coordinates, with "r" being the radial variable and "z" being the normal variable. The angular variable "theta" does not need to be included in the problem because the physics of the problem assure cylindrical symmetry; therefore, there is no angular dependence to any function. The variable "u" represents the displacement in the radial direction, and "w" is the displacement in the normal direction.

Case 1 is a rigidly clamped boundary condition where the slope of the normal displacement of the blister at its bottom surface is zero at the blister's edge, r=b, and the center of the plate is the neutral plane. Case 2 uses the boundary condition of no net bending moment along the outer edge of the blister and a neutral center plane to model a simply supported disk. For case 3, the radial displacement, u, equals 0 at both the top surface and the bottom surface of the blister at its edge r=b, an alternative model for a rigidly clamped plate. Case 4 is a solution using mixed boundary conditions. The first boundary condition is that the radial displacement, u, equals 0 at the outer edge of the disk at the bottom surface (r=b, z=h/2), and the second boundary condition is that the radial stress $\sigma_r=0$ at the top, outer edge (r=b, z=h/2). It is reasonable to expect the deformation of the transparent coat to be somewhere between a rigidly clamped and simply supported plate, since these are the two extremes of boundary conditions. Therefore, case 4 is preferred.

In addition to the four cases described above, the bending of a thick plate, case 5, can also be considered. (See S. Timoshenko, S. Woinowsky-Krieger, *Theory of Plates and Shells*, McGraw-Hill, New York, 1959, p. 74).

After the initial curvature of the blister at the critical pulse energy has been determined, a critical internal pressure of the blister at the critical pulse energy is determined. For all cases 1–5, a relationship, at any pulse energy, between internal pressure and the initial curvature of a blister has been developed herein and can be summarized by:

$$q = \frac{16D}{R_c b^2} [k_1 + k_2(h/b)^2]^{-1} \quad \text{Equation (3)}$$

wherein:

D is the flexural rigidity of the transparent topcoat;

$$D = \frac{Eh^3}{12(1-\upsilon^2)} ; \quad \text{Equation (4)}$$

E is the modulus of the transparent topcoat;

υ is Poisson's ratio of the transparent topcoat;

h is the thickness of the transparent topcoat;

b is the blister radius;

$R_c$ is the measured initial radius of curvature of the blister; and $k_1$ and $k_2$ are constants depending on the particular boundary conditions selected, e.g. case 1–5.

Figure 4:
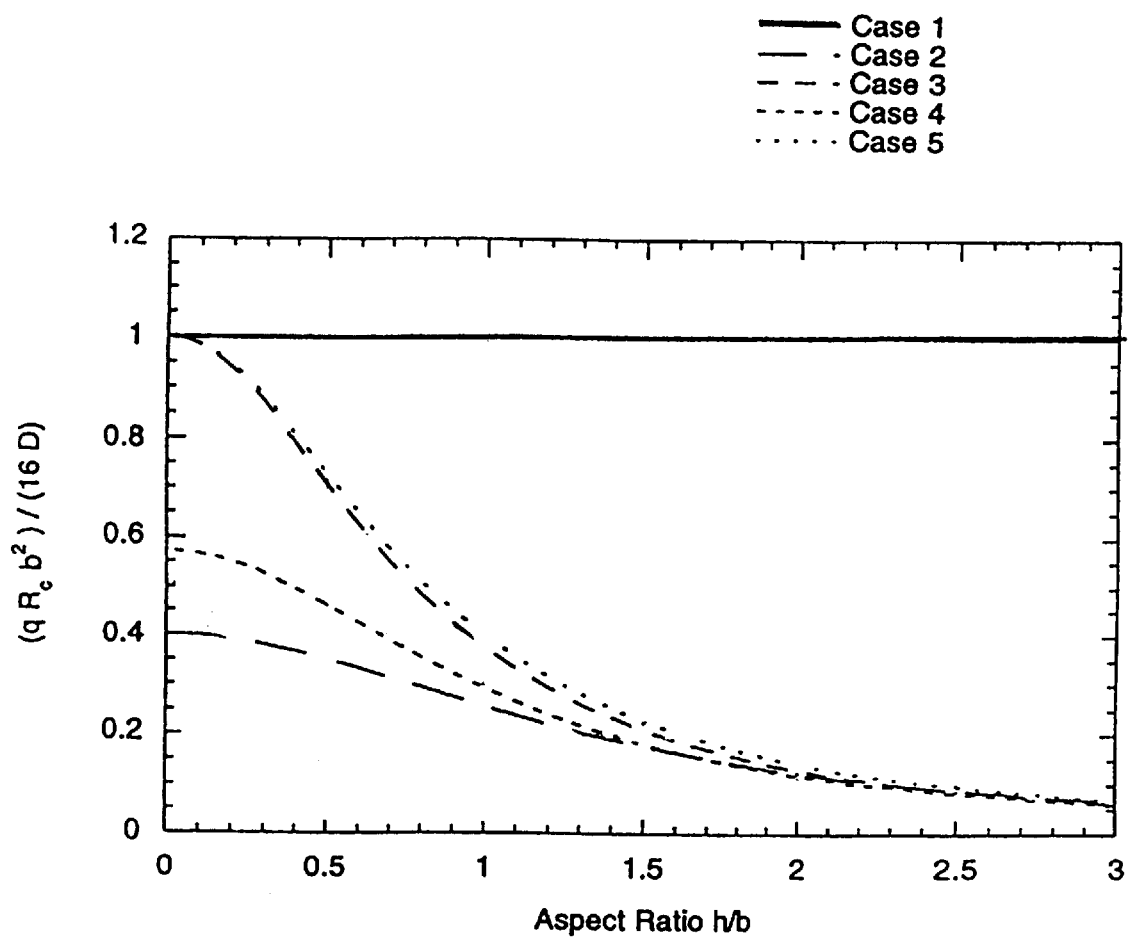
FIG. 4 is a graphical representation of the dimensionless parameter $qR_c b^2/16D$ as a function of the aspect ratio (h/b) for various theoretical boundary conditions.

FIG. 4 is a graphical representation of the dimensionless parameter $qR_c b^2/16D$ (which is equal to the second factor of Equation 3) as a function of aspect ratio for all five cases, assuming $\upsilon = 1/3$. It represents a slight rearrangement of Equation 3 for different values of $k_1$ and $k_2$ and shows how the different constants effect the curve. Case 4 represents the preferred boundary conditions.

Herein, E=3 GPa is used as the modulus, which is the −150° C., 10 Hz value obtained from dynamic mechanical analysis (DMA) experiments on a typical automotive clearcoat, Gen4. This low temperature, low frequency value is expected to be appropriate for the response of the polymer based on the fast rise time of a blister formed therein (about 100 ns) and the time-temperature superposition principle. (See Viscoelastic Properties of Polymers by John D. Ferry, Wiley and Sons, New York, 1980, p. 280).

For Poisson's ratio of the transparent coat, υ, a value of 1/3 has been assumed herein as reasonable for these materials. Other values may be appropriate for other materials.

The thickness of the transparent coat, h, can be measured by end polishing the coating system and then measuring the coating thicknesses with a microscope reticle. (See Example 42, Col. 5, for example). Other means for measuring the thickness of the transparent coat will be obvious to those of ordinary skill in the art.

The blister radius, b, can be measured using an optical microscope with a dark field illumination and a calibrated reticle and looking at laser exposures just slightly below the critical pulse energy. Values for the radius of the blister for several regions of a sample can be averaged together. (See Example 42, Col. 6, for example).

In Table 1 below, the constants, $k_1$ and $k_2$, for cases 1–5 are collected.

TABLE 1

| Boundary Conditions | $k_1$ | $k_2$ |
|---|---|---|
| case 1 - clamped thin plate | 1 | 0 |
| case 2 - simply supported disk | $\frac{(3+\upsilon)}{(1+\upsilon)}$ | $\frac{4(2+\upsilon)}{5(1+\upsilon)}$ |
| case 3 - clamped disk | 1 | $\frac{2(2-\upsilon)}{3(1-\upsilon)}$ |
| case 4 - mixed | $\frac{(2+\upsilon)}{(1+\upsilon)}$ | $\frac{2(2-\upsilon)}{3(1-\upsilon)}$ |

TABLE 1-continued

| Boundary Conditions | $k_1$ | $k_2$ |
|---|---|---|
| case 5 - thick plate | 1 | $\frac{2}{(1-\upsilon)}$ |

Thus, by substituting in the measured and determined values for the variables in Equation 3, the critical internal pressure of the blister at the critical pulse energy can be determined. (See Example 42, col. 8, for example.)

Finally, the internal pressure of the blister at the critical pulse energy is related to an adhesion parameter, G, to determine the adhesion of the film system. A relationship between the dimensionless parameter $q^2 b/(E \cdot G)$ and the aspect ratio h/b is derived herein for the boundary conditions, cases 1–4. (See S. J. Bennett, K. L. DeVries, M. L. Williams, Int. Journ. of Fracture, 10, 33 (1974)). This relationship can be characterized by a function f(h/b). For small h/b, $f(h/b) \cong (h/b)^3$ as predicted by plate theory, and f(h/b) approaches a constant for large h/b, in accordance with the theory for an infinite solid (see I. N. Sneddon, M. Lowengrub, *Crack Problems in the Classical Theory of Elasticity*, Wiley, New York, 1969, p. 134, and Bennett et al. Ibid.). In order to derive f(h/b) for the present invention, the total strain energy in the system is calculated by integration of the proper combination of stress/strain (See S. Timoshenko, J. N. Goodier, *Theory of Elasticity*, McGraw-Hill, New York, 1970). This energy is differentiated with respect to crack area and the terms rearranged. The strain energies (far-field energies) for cases 1–4, are calculated, and the result for case 5 is taken from the work of E. H. Andrews and A. Stevenson (Journ. Mat. Sci., 13, 1680 (1978)). To the far-field energy is added the strain energy surrounding the crack tip (the near-field energy), taken from the work of Sneddon(Ibid.). Then f(h/b) can be expressed as a polynomial with constant coefficients:

$$f(h/b) = \frac{(h/b)^3}{a_1 + a_2(h/b)^2 + 16/9\pi(h/b)^3} \quad \text{Equation (6)}$$

Figure 5:
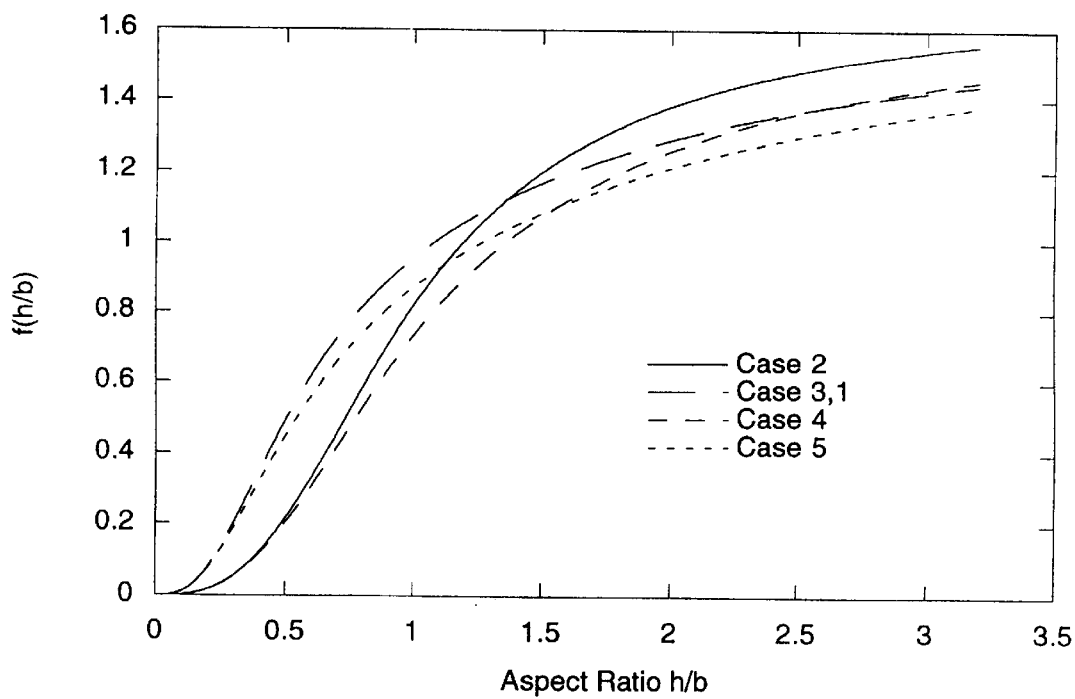
FIG. 5 is a graphical representation for the function f(h/b), relating the internal pressure of a blister to the work of adhesion for various theoretical boundary conditions. (See Equation 7 below).
Figure 6A:
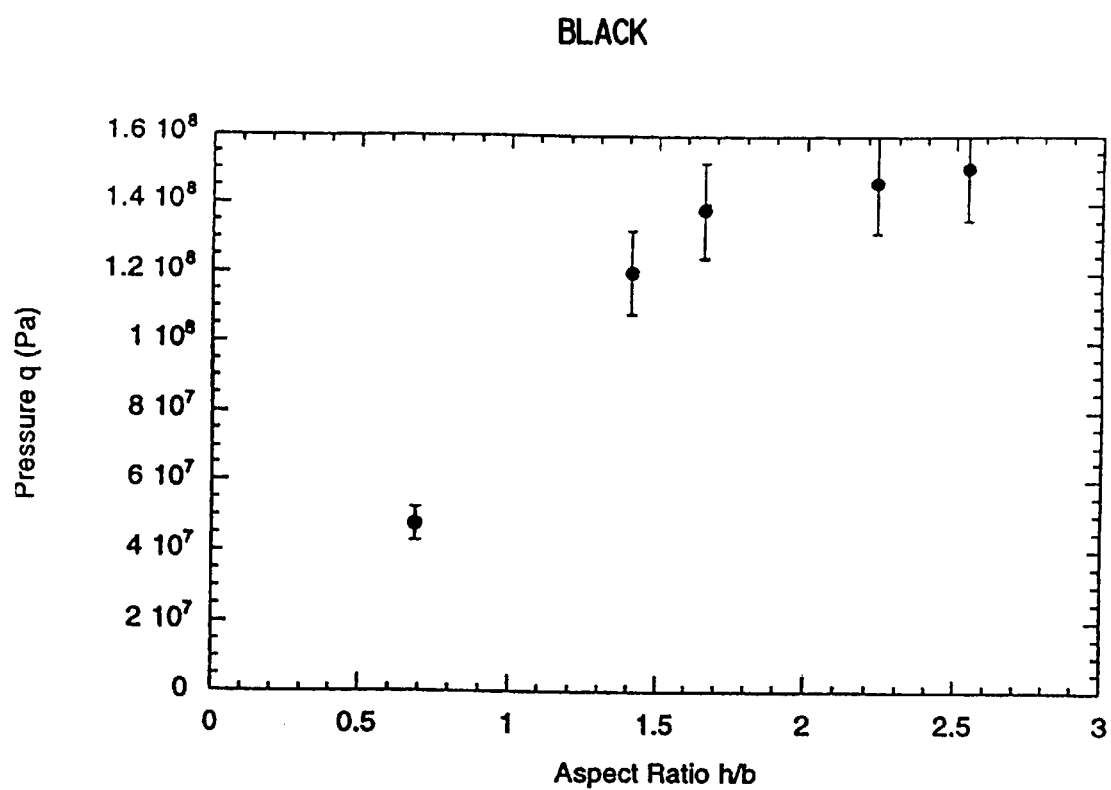
FIGS. 6A–6D show the critical pressure required for debonding versus aspect ratio for systems exemplified herein. (See Examples 9–24 for FIG. 6A, Examples 25–34 for FIG. 6B, 35–47 for FIG. 6C, and Examples 48–61 for FIG. 6D.)
Figure 6B:
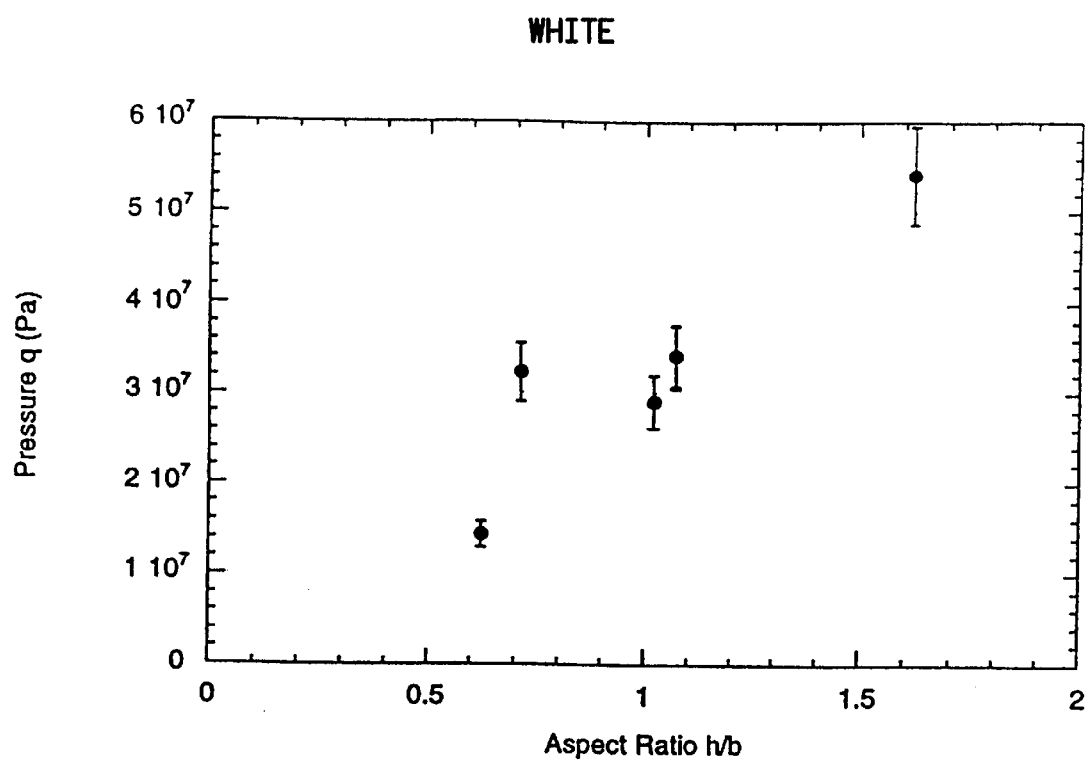
Figure 6C:
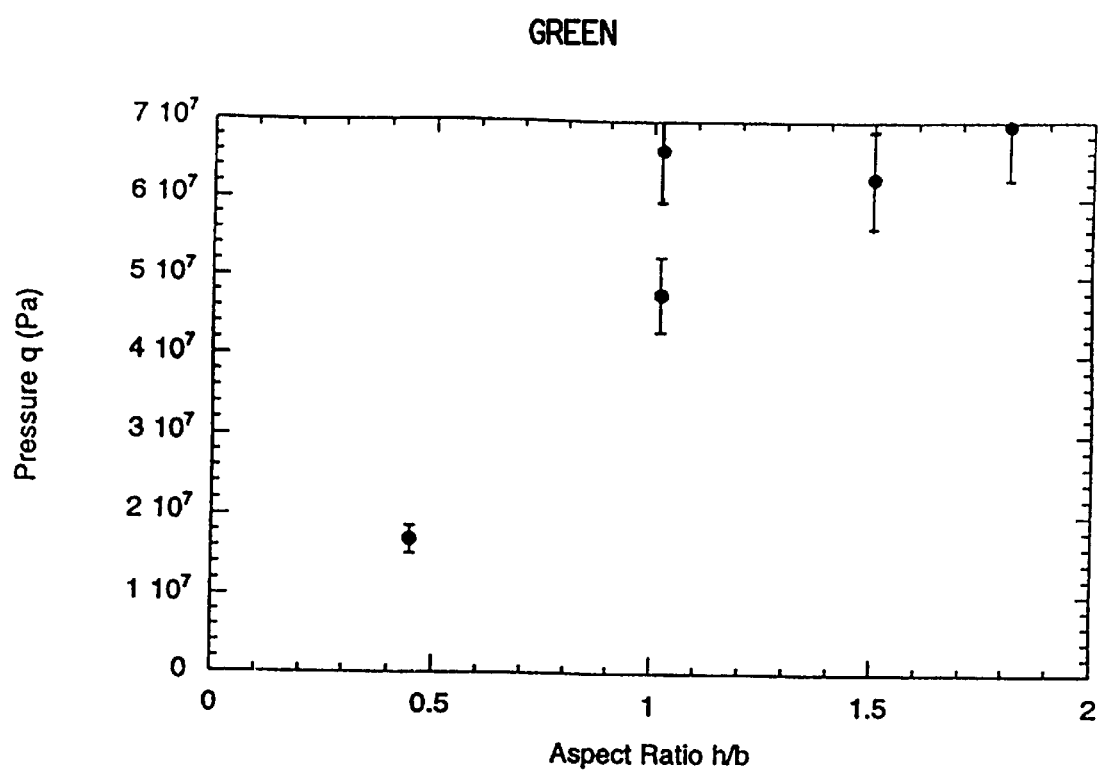
Figure 6D:
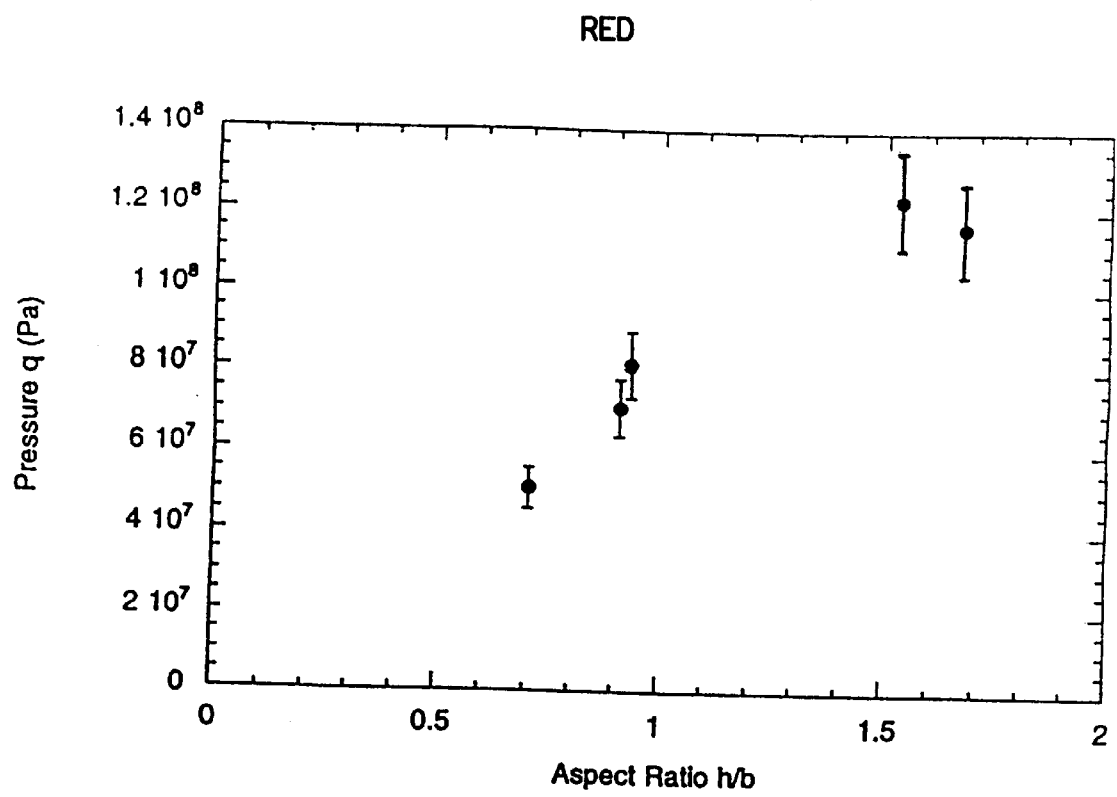
Figure 7A:
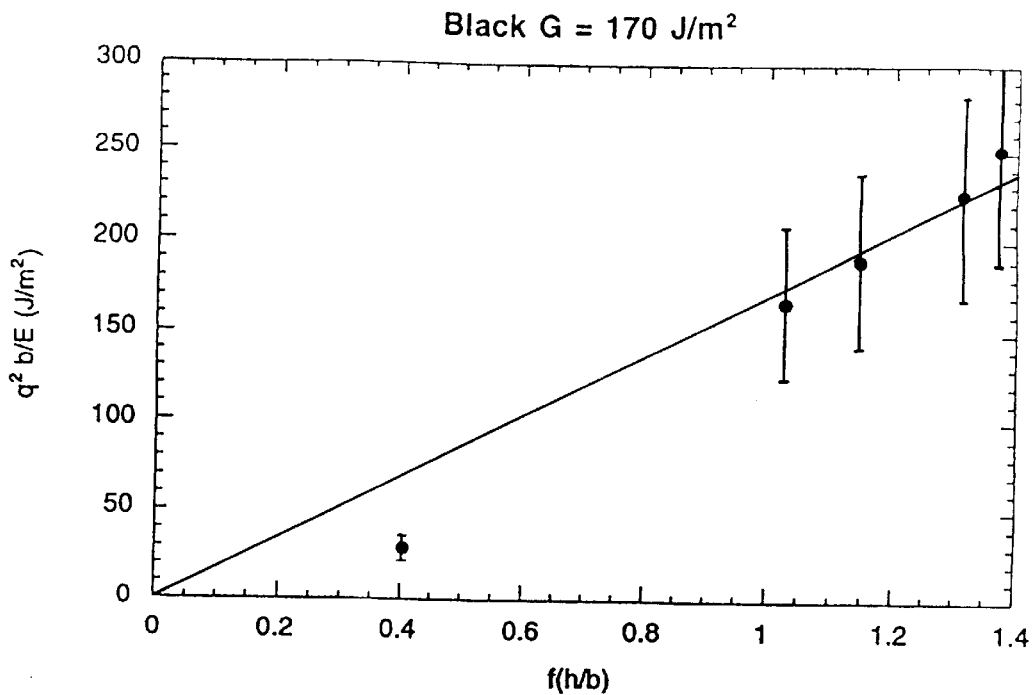
FIGS. 7A–7D show a linear plot of $q^2 b/E$ versus f(h/b) for four basecoat colors. The slopes are interpreted as the practical work of an adhesion parameter, G. (See Examples 9–24 for FIG. 7A, Examples 25–34 for FIG. 7B, 35–47 for FIG. 7C, and Examples 48–61 for FIG. 7D.) For FIG. 7A, the slope is 169.88 with a standard error of 9.0363. The Chi square value is 2002.2 and Pearson's R value is 0.96613. For FIG. 7B, the slope is 27.286 with a standard error of 4.6281. The Chi square value is 236.37 and Pearson's R value is 0.82576. For FIG. 7C, the slope is 65.337 with a standard error of 4.5179. The Chi square value is 426.51 and Pearson's R value is 0.92626. For FIG. 7D, the slope is 176.48 with a standard error of 22.986. The Chi square value is 10977 and Pearson's R value is 0.85189.
Figure 7B:
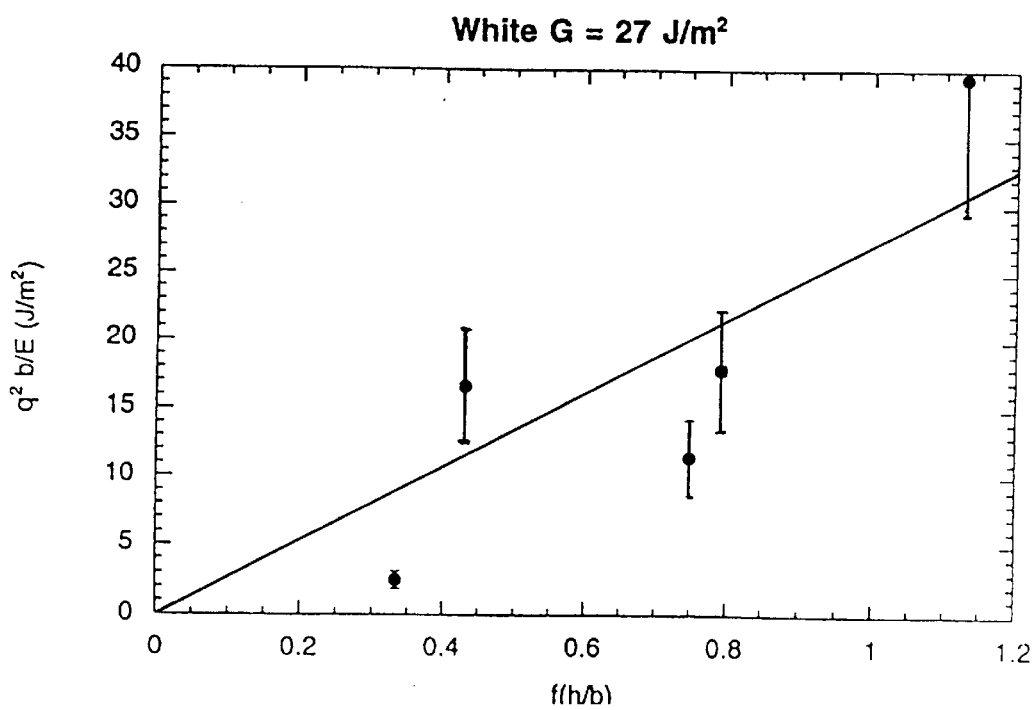
Figure 7C:
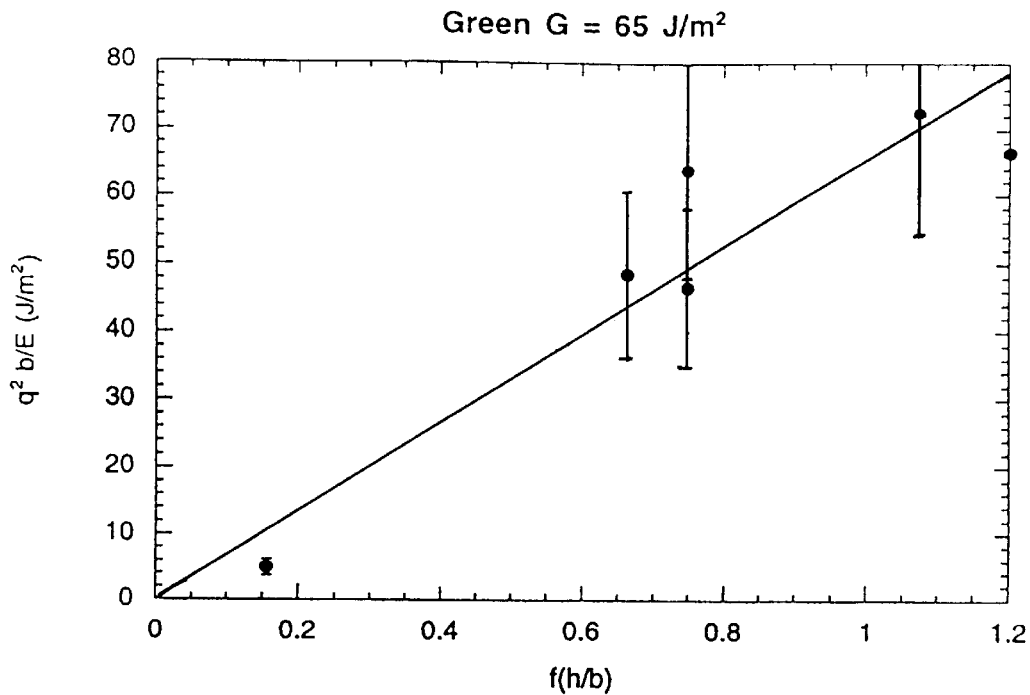
Figure 7D:
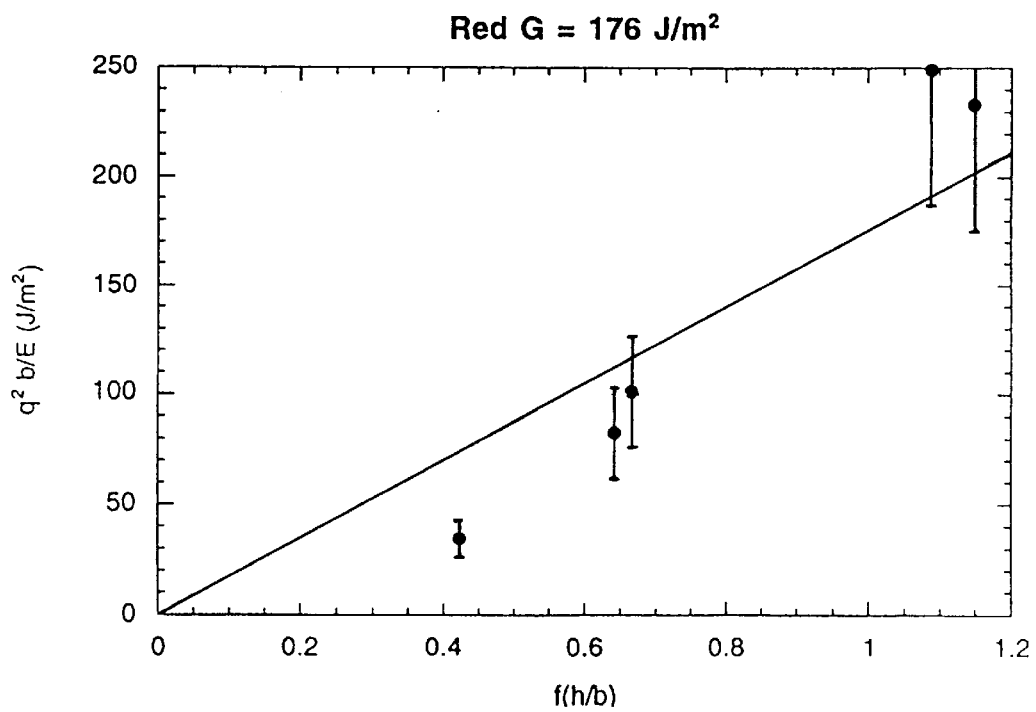

The values of $a_1$ and $a_2$ depend on the boundary conditions. Table 2 below collects the various values from the different cases, and in FIG. 5 these functions are displayed graphically. Preferably, $a_1$ is 11/24 and $a_2$ is 31/90.

TABLE 2

| Boundary Condition | $a_1$ | $a_2$ |
|---|---|---|
| case 1, 3 | 1/12 | 2/5 |
| case 2 | 11/24 | 1/5 |
| case 4 | 11/24 | 31/90 |
| case 5 | 1/12 | 1/2 |

Finally, $q^2 b/E$ vs. f(h/b) can be plotted. The straight line fit to this plot has the adhesion parameter, G, as its slope. Thus, $$G = \frac{q^2 b}{E f(h/b)} \quad \text{Equation (7)}$$

wherein q is the internal blister pressure at the critical pulse energy.

For film systems where it is not possible to plot $q^2 b/E$ vs. f(h/b), Equations 3 and 7 can be combined to give:

$$G = \frac{16E}{9(1-\upsilon^2)^2} \frac{h^3}{R_c^2} g(h/b) \qquad \text{Equation (8)}$$

Figure 8:
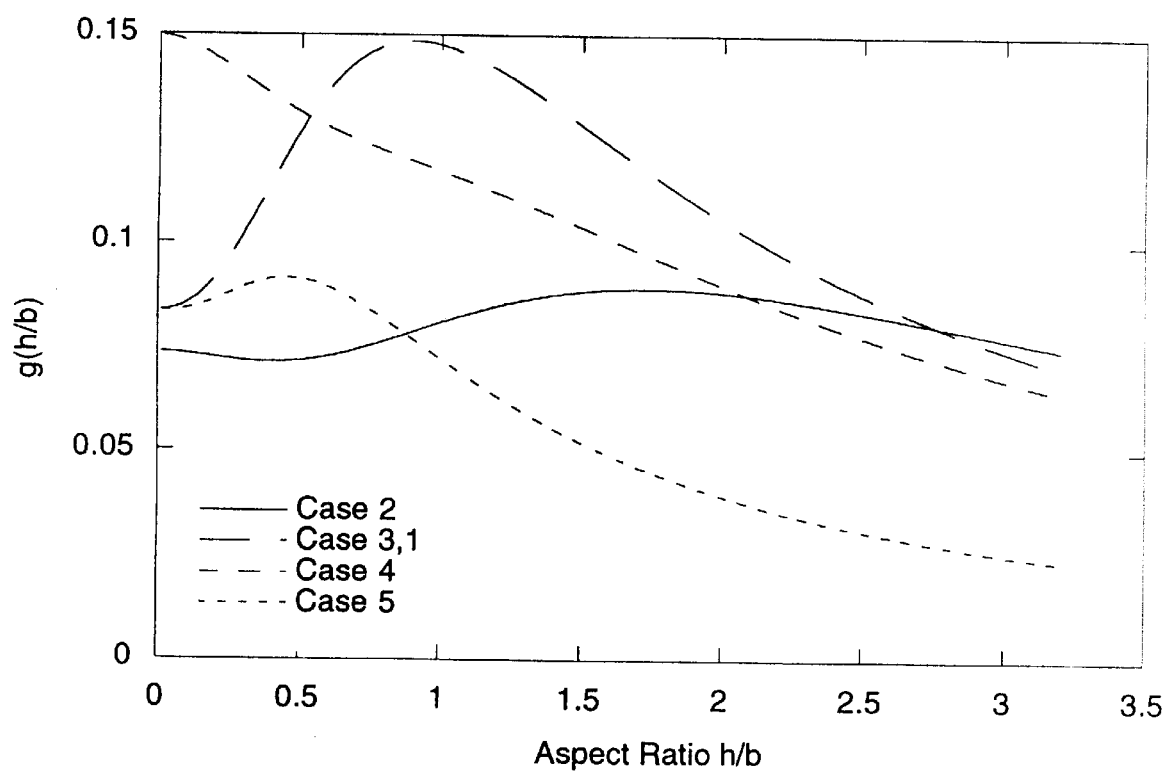
FIG. 8 is a graphical representation of g(h/b) versus aspect ratio for various theoretical boundary conditions.

For this embodiment, the determination of the adhesion parameter, G, is dependent on three factors. The first factor depends on the material parameters E and v. The second factor depends on experimentally determined variables h and $R_c$. The third factor depends on the aspect ratio of the blister and is dependent on the particular boundary condition selected. In FIG. 8, g(h/b) is plotted versus aspect ratio for cases 1–5. It should be noted that g is a smooth function whose magnitude does not change drastically over aspect ratio, or for the different cases 1–5.

The adhesion parameter is used herein to determine the adhesion of the film system. Large values of G mean better adhesion than small values of G. Thus, the present invention further permits the quantitative comparison of adhesion of two different film systems.

The process of the present invention is useful in testing the adhesion of multilayer paint systems, such as automotive finishes. Of particular value is the analysis of the G values for different automotive paint formulations to yield the relative adhesion of a coating system, for example, an opaque coat, such as an electrocoat, primer or colored basecoat, having applied thereon a transparent coat, such as an unpigmented primer, unpigmented basecoat or clear topcoat. Thus, an important purpose of determining the adhesion of a film system is to be able to perform a physical process—i.e., comparing the parameter of one film system to that of another film system to identify quantitatively the one that possesses superior adhesion properties. In this way, particular polymers formulations, additives and process conditions can be identified as contributing to a coating that exhibits better adhesion. Communication of the results of these comparison can result in adjustments to the ingredients and/or process conditions for making film systems resulting in film systems with improved adhesion. Thus, the process of the present invention in addition to determining the adhesion of a film system can further comprise improving the adhesion of a film system by further comprising the steps of: comparing the adhesion parameter of one film system with the adhesion parameter of a second film system which differs from the first film system in a variable to identify the film system possessing a higher value for the adhesion parameter, and adjusting the preparation of a third film system to incorporate or substitute for another variable, the variable of the first or second film system possessing the higher value for the adhesion parameter to improve the adhesion of the third film system. The variable can be one or more ingredients, additives, formulations, or processing conditions; such as bake conditions, e.g. time for baking temperature, or type of over; method of coating; or other processing conditions known to those of skill in the art. Preferably, the first and second film systems differ in only one variable. The third film system differs from the first or second film system having the higher G value in at least the variable of difference between the first and second film system. Preferably, the third film system has the same variable as the first or second film system possessing the lower G value, and the variable of the first or second film system possessing the higher G value is then substituted into the third film system for the variable of the film system possessing the lower G value.

EXAMPLES

The following abbreviations are used for Examples 1–61:
WBBC=CROMAX® Waterborne basecoat, available from E. I. du Pont de Nemours and Company of Wilmington, Del., comprised of
16.5% pigment
13.7% polyester resin
33.8% latex
8.9% polyester urethane (aliphatic)
14.5% melamine
12.6% dispersant aids, ultraviolet (UV) screeners, etc.
CC=GEN4 clearcoat, available from E. I. du Pont de Nemours and Company, comprised of
44% melamine acrylate resin
56% acrylo-silane resin Samples for Examples 1–61 were prepared by coating a stainless steel panel with an electrocoat, CORMAX®, available from E. I. du Pont de Nemours and Company, 768C primer, available from E. I. du Pont de Nemours and Company, and WBBC. The panel was then flashed for 5 min at 80° C. to drive off the water solvent. The CC was sprayed on top of the WBBC. The panel was then cured in an oven, with air flow, for 30 min at 130° C.

It is known to those skilled in the art that polymeric coatings generally show a decrease in adhesion to other coatings, as well as to substrates, with an increase in exposure to UV radiation or humidity cabinet conditions. There is generally a drop-off of adhesion after a certain number of cycles, or hours. For example, visual loss of adhesion as seen by delamination generally occurs between 4000 and 6000 hours in a QUV test. An advantage of the present method is that it allows the detection of loss of adhesion between 1000 and 2000 hours, therefore in less than half the time. Also, because the present method involves actual measurements and therefore is quantitative, the data obtained is more reliable than that obtained with a qualitative, visual test.

The following exposure protocols or tests were used in Examples 1–61:

QUV Test

This test is based on ASTM G-53. The QUV testing equipment is available from Q Panel, Troy, Mich. In stage 1, the coated panels were exposed to UV for 4 hours at 60° C., using UVA-340 bulbs. The panels were rotated using the standard protocol found in ASTM G-53. In stage 2, the panels were exposed at condensation conditions for 4 hours at 40° C. The panels were cycled between stages 1 and 2 for the total elapsed exposure time.

UV-only Test

The coated panels were exposed to UVA-340 bulbs at 60° C. for the total elapsed time.

140 CHC Test

The coated panels were exposed to 100% humidity at 140° F. using a Cleveland Humidity Cabinet (CHC). This is also known as condensation exposure.

Two lasers were used. The first laser was an ablating laser which created the blister. The laser wavelength was 1053 nm, and the pulse width was 50 ps. A single pulse from the laser was injected into a regenerative oscillator cavity running at 10 Hz using a Pockels cell. The regenerated pulse was then cavity dumped with a second Pockels cell. The laser pulse then passed through a vacuum spatial filter to produce a Gaussian spatial profile. The beam then went through a combination quarter-wave plate, half-wave plate and polarizer which allowed precise adjustments of the laser pulse energy, as recorded by a Molectron joulemeter Model JD-1000, available from Molectron Detector Inc., Portland, Oreg.

The laser pulse energy obtained without the preamplifier or amplifier stages was about 1 mJ. Most of the experiments were performed at pulse energies between 50–200 μJ. The laser output energy was stable to within 3%. There were two shutters in the beam path of the laser. One was a manual shutter and the second was an automatic shutter. Since each spot on the sample could only be exposed once, it was necessary to be able to separate out a single pulse from the 10 Hz pulse train as desired. The automatic shutter allowed one pulse in forty (adjustable) to pass through, which provided the experimental operator with sufficient time to open and close the manual shutter when an experiment was performed. The laser was then focused onto the sample by an f=20 cm lens to a $1/e^2$ intensity radius of 50 μm.

The samples were mounted vertically on a translation state that was motorized in the x-direction (across) and manual in the y-direction (up/down). The motorized state could be positioned reproducibly to 1 μm via computer control. The z-dimension was fixed to be the focal plane of the lens focusing the IR laser pulse. A blister was formed by exposing the sample to a single IR laser pulse. The sample was then translated 1.5 mm before another laser pulse was incident on the sample. No position on the sample was ever exposed to more than a single laser pulse for data acquisition. Data was collected from three regions, top, middle and bottom, of the plate to reduce any possible contributions due to clear coat thickness variations over the area of the plate. The second laser was a low power, continuous wave HeNe laser used to determine the initial radius of curvature of the blister at the critical pulse energy.

Tables 3–8 present the data collected in the following examples. The columns represent values for the following:

Col. 1: critical pulse energy (μJ)

Col. 2: slope of the line plotted for pulse energy vs. initial curvature of the blister, $1/R_c$ Col. 3: intercept of the line plotted for pulse energy vs. $1/R_c$ Col. 4: $1/R_c$ at the critical pulse energy Col. 5: average thickness of the transparent topcoat, h (μm)

Col. 6: average radius of the blister, b, (μm)

Col. 7: aspect ratio (h/b)

Col. 8: internal pressure of the blister, q, at the critical pulse energy calculated from Equation 3

Col. 9: adhesion parameter, G, (J/m$^2$), from Equation 7 or Equation 8

Col. 10: critical internal blister pressure squared times the blister radius divided by the modulus, $q^2b/E$ Col. 11: value of Equation 6 for the aspect ratio of the experiment, f(h/b).

"Top", "mid", and "bot" as used in the Sample Column refer to the position of the blister on the panel. "Across" refers to a sample turned 90°, and "re" refers to a repeated experiment.

Examples 1–8

Samples of standard red WBBC coated with a CC were prepared. As shown in the column labeled "Sample" of Table 3, the samples were exposed in various ways (UV, QUV, CHC) for various times, and then characterized using the process of the present invention. The adhesion parameter, G, was determined for these examples and is shown in Column 9 of Table 3.

Examples 9–61

These examples, also summarized in Table 3, represent different color basecoats, and different thicknesses of clearcoats. These samples were not exposed as were those in Examples 1–8; rather, the measurements by the process of the present invention were made on unexposed samples. FIGS. 6A–6D are graphical representations showing the critical pressure required for debonding versus aspect ratio, FIG. 6A for Examples 9–24, FIG. 6B for Examples 25–34, FIG. 6C for Examples 35–47, and FIG. 6D for Examples 48–61. FIGS. 7A–7D show a linear plot of q2b/E versus f(h/b) wherein the slope is interpreted as the practical work of the adhesion parameter, FIG. 7A for Examples 9–24, FIG. 7B for Examples 25–34, FIG. 7C for Examples 35–47, and FIG. 7D for Examples 48–61. The adhesion parameter, G, was determined for these examples and is shown in Column 9 of Table 3.

In the examples that follow, the electrocoat is CORMAX®, the primer is 768C, the basecoat is CROMAX® and the clearcoat is GEN4, unless otherwise indicated.

Examples 62–127

Unpolished cold rolled steel was electrocoated, a 1.0–1.2 mil gray primer was applied, flashed for 10 min and baked for 30 min at 265° F. and solvent wiped. A red or burgundy waterborne basecoat, CROMAX®, was applied over the primer, flashed and baked for 5 min at 180° F. A 2.0–2.4 mil clear coat, GEN4 Clear, was applied over the basecoat, flashed and baked for 30 min at 265° F. Formulation changes were made in the basecoat as follows:

| Example Numbers | Pigment Type | Auxiliary Polymer | Surfactant Type | Latex (Acrylic) |
| --- | --- | --- | --- | --- |
| 62–65 | coarse | acrylic | Surfynol ® 104 | No. 1* |
| 66–68 | fine | acrylic | Foamacure ® 281 | No. 3 |
| 69–72 | fine | acrylic | Foamacure ® 281 | No. 1 |
| 73–75 | fine | acrylic | none | No. 3 |
| 76–79 | coarse | polyester | none | No. 3 |
| 80–82 | fine | polyester | Surfynol ® 104 | No. 3 |
| 83–86 | fine | polyester | Foamacure ® 281 | No. 2 |
| 87–90 | fine | polyester | none | No. 2 |
| 91–93 | coarse | polyester | Foamacure ® 281 | No. 1 |
| 94–96 | fine | polyester | Surfynol ® 104 | No. 1 |
| 97–99 | coarse | polyester | Foamacure ® 281 | No. 3 |
| 100–102 | fine | acrylic | Surfynol ® 104 | No. 3 |
| 103–105 | coarse | acrylic | Surfynol ® 104 | No. 2 |
| 106–109 | fine | polyester | none | No. 1 |
| 110–118 | coarse | acrylic | none | No. 2 |
| 119–121 | coarse | polyester | none | No. 3 |
| 122–124 | fine | acrylic | Foamacure ® 281 | No. 1 |
| 125–127 | fine | polyester | none | No. 1 |

*Refers to the final structure of each succeeding monomer introduced to prepare the spheres in the latex component of the basecoat
No. 1 is a crosslinked core, crosslinked core, and uncrosslinked shell
No. 2 is a crosslinked core and uncrosslinked shell
No. 3 is a crosslinked core and uncrosslinked shell Examples 62–115 were exposed in the open air in Florida for one year, and Examples 116–127 were unexposed (unexp). Measurements were performed on the clearcoat/basecoat interface and are summarized in Table 4. The adhesion parameter, G, was determined for Examples 62–127 and is shown in Col. 9 of Table 4.

Examples 128–148

Unpolished cold rolled steel was first electrocoated. For Examples 128–130, the electrocoated steel was coated with primer (768C) and then with a GEN 3 Clearcoat (GEN3) available from E. I. du Pont de Nemours and Company. For Examples 131–139, 768C primer was applied to the electrocoat and then a clear basecoat, unpigmented CROMAX®

(CRO) was applied. For Examples 140–148 20% urethane beads (by weight) pigment (UBP) primer was applied over the electrocoat and then the unpigmented CROMAX® was applied. Baking conditions were as follows:

| Examples | Time   | Temperature |
|----------|--------|-------------|
| 131–133  | 30 min | 240° F.     |
| 134–136  | 30 min | 285° F.     |
| 137–139  | 60 min | 380° F.     |
| 140–142  | 60 min | 380° F.     |
| 143–145  | 30 min | 285° F.     |
| 146–148  | 30 min | 240° F.     |

Measurements were performed on the basecoat/primer interface and are summarized in Table 5. The adhesion parameter, G, was determined for these examples and is shown in Col. 9 of Table 5.

Examples 149–187

Unpolished cold rolled steel was electrocoated and a 536C primer surfacer (536C), available from E. I. du Pont de Nemours and Company, applied. A waterborne basecoat, CROMAX®, was spray applied at 0.8–1.0 mils and baked at 180° F. A GEN 4A clearcoat was spray applied at 2.0–2.4 mils and baked at 265° F. Certain panels were exposed in the open air in Florida for 12 months and were designated "bfc" (exp); those that were not exposed were designated "bfa" (unexp). The "bfc" exposed and "bfa" unexposed panels were made at the same time. WBBC was the waterborne basecoat used. DW-1 Red and Masstone Red differ slightly from Red WBBC in pigment/color formulation. HSBC is a high solids solvent borne basecoat; and 2K is an isocyanate clearcoat. Additional codes used in Table 6 are as follows:

| Panel No. | Basecoat          | Clearcoat |
|-----------|-------------------|-----------|
| 4         | Red HSBC          | GEN4A     |
| 6         | DW-1 Red WBBC     | GEN4A     |
| 7         | Red WBBC          | GBN3      |
| 9         | Red WBBC          | GEN4A     |
| 10        | Red WBBC          | 2K        |
| 13 (BFC)  | Masstone Red WBBC | GEN4A     |
| 14        | Red WBBC (no black) | GEN4A   |

Measurements were performed on the clearcoat/basecoat interface and are summarized in Table 6. The adhesion parameter, G, was determined for these examples and is shown in Col. 9 of Table 6.

Examples 188–235

Phosphated cold rolled steel was electrocoated with CORMAX® with anticratering additives added. ACA #1 (#1) is a mixture of Epon 1001, methylethanol amine, and Jeffamine® D-2000 (from Texaco) in a 1:1:1 molar ratio with Epon 828, Jeffamine® D-2000, diketimine, and aminopropyltriethoxysilane condensed together. ACA #2 (#2) contains Jeffamine® D-2000 and isocyanatopropyltrimethoxysilane in a 1:2 mole ratio. The baking conditions used for both gas and electric are shown below. A clear primer was applied at 1.0 mil over the electrocoat. Measurements were performed on the electrocoat/primer interface and are summarized in Table 7. The adhesion parameter, G, was determined for these examples and is shown in Column 9 of Table 7.

| Example | Electrocoat | Bake (Time, Temp & Type)  |
|---------|-------------|---------------------------|
| 188–190 | ACA #1      | 17 min, 330° F., Gas      |
| 191–193 | ACA #1      | 17 min, 330° F., Electric |
| 194–196 | ACA #1      | 17 min, 360° F., Gas      |
| 197–199 | ACA #1      | 17 min, 360° F., Electric |
| 200–202 | ACA #1      | 17 min, 390° F., Gas      |
| 203–205 | ACA #1      | 17 min, 390° F., Electric |
| 206–208 | ACA #1      | 30 min, 390° F., Gas      |
| 209–211 | ACA #1      | 30 min, 390° F., Electric |
| 212–214 | ACA #2      | 17 min, 330° F., Gas      |
| 215–217 | ACA #2      | 17 min, 330° F., Electric |
| 218–220 | ACA #2      | 17 min, 360° F., Gas      |
| 221–223 | ACA #2      | 17 min, 360° F., Electric |
| 224–226 | ACA #2      | 17 min, 390° F., Gas      |
| 227–229 | ACA #2      | 17 min, 390° F., Electric |
| 230–232 | ACA #2      | 30 min, 390° F., Gas      |
| 233–235 | ACA #2      | 30 min, 390° F., Electric |

Examples 236–240

For Examples 236–238 substrates of thermoplastic olefin (TPO), Himont TPO ETA 3183, were coated with Refinish 7500 clearcoat, available from E. I. du Pont de Nemours and Company. Example 236 was the control. Example 237 was sanded by hand with 600 grit sandpaper. Example 238 was the same as 237 but 400 grit sandpaper was used. Example 239 was another control of TPO coated with IMRON® 3440S, available from E. I. du Pont de Nemours and Company. Example 240 was sandblasted with STARBLAST®, available from E. I. du Pont de Nemours and Company. Baking conditions were for 30 min. at 265° F. Measurements were performed on the clearcoat/TPO interface and are summarized in Table 8. The adhesion parameter, G, was determined for Examples 236–240 and is shown in Col. 9 of Table 8.

TABLE 3

| Ex. | Sample | 1 Ctri. En. (uJ) | 2 Slope | 3 Intercept | 4 1/Rc | 5 Thickness h | 6 Radius b | 7 Aspect Ratio (h/b) | 8 Pressure q | 9 G (J/m$^2$) |
|---|---|---|---|---|---|---|---|---|---|---|
| 1  | QUV, 500 hrs.     | 215.00 | 12.895 | 1202.2 | 1570.2 | 38.100 | 43.960 | 0.86670 | 6.7365e+07 | 67.509  |
| 2  | QUV, 1000 hrs.    | 197.00 | 16.351 | 1588.5 | 1632.6 | 38.100 | 44.060 | 0.86473 | 6.9857e+07 | 72.945  |
| 3  | QUV, 2000 hrs.    | 180.00 | 11.057 | 1128.7 | 861.56 | 38.100 | 38.890 | 0.97969 | 4.2325e+07 | 20.788  |
| 4  | UV, 500 hrs.      | 205.00 | 8.5747 | 670.24 | 1087.6 | 38.100 | 43.750 | 0.87086 | 4.6919e+07 | 32.421  |
| 5  | UV, 2000 hrs.     | 210.00 | 12.221 | 1367.6 | 1198.8 | 38.100 | 43.650 | 0.87285 | 5.1855e+07 | 39.412  |
| 6  | UV, 2000 hrs.     | 163.00 | 10.675 | 982.77 | 757.26 | 38.100 | 40.000 | 0.95250 | 3.6109e+07 | 15.992  |
| 7  | 140-CHC, 1000 hrs.| 183.00 | 15.168 | 1832.4 | 943.34 | 38.100 | 39.900 | 0.95489 | 4.5103e+07 | 24.828  |
| 8  | 140-CHC, 2000 hrs.| 170.00 | 10.253 | 1156.2 | 586.81 | 38.100 | 39.690 | 0.95994 | 2.8215e+07 | 9.6149  |
| 9  | 1.5 mil black     | 190.00 | 11.299 | 440.39 | 1706.4 | 49.700 | 28.400 | 1.7500  | 1.7052e+08 | 168.48  |
| 10 | 1.5 mil black (top)| 148.00 | 11.354 | 217.25 | 1463.1 | 49.700 | 30.000 | 1.6567  | 1.4201e+08 | 126.36  |
| 11 | 1.5 mil black (mid)| 150.00 | 11.489 | 168.32 | 1555.0 | 49.700 | 32.500 | 1.5292  | 1.4401e+08 | 146.25  |
| 12 | 1.5 mil black (bot)|        |        |        |        | 49.700 |        |         |            |         |
| 13 | 1.7 mil black (top)| 115.00 | 12.451 | 126.50 | 1305.4 | 49.000 | 33.900 | 1.4454  | 1.1494e+08 | 100.12  |

TABLE 3-continued

| Ex. | Sample | 1<br>Ctrl. En. (uJ) | 2<br>Slope | 3<br>Intercept | 4<br>1/Rc | 5<br>Thickness h | 6<br>Radius b | 7<br>Aspect Ratio (h/b) | 8<br>Pressure q | 9<br>G (J/m²) |
|---|---|---|---|---|---|---|---|---|---|---|
| 14 | 1.7 mil black (bot) | 115.00 | 13.721 | 119.92 | 1458.0 | 49.000 | 35.000 | 1.4000 | 1.2560e+08 | 125.70 |
| 15 | 1.7 mil black (across) | 165.00 | 9.4479 | 174.75 | 1384.2 | 49.000 | 35.200 | 1.3920 | 1.1877e+08 | 113.41 |
| 16 | 3.0 mil black (bot) | 150.00 | 6.5923 | 103.69 | 885.15 | 71.000 | 29.500 | 2.4068 | 1.4365e+08 | 112.21 |
| 17 | 3.0 mil black (mid) | 146.00 | 8.2309 | 275.20 | 926.51 | 71.000 | 32.300 | 2.1981 | 1.4591e+08 | 129.78 |
| 18 | 3.0 mil black (top) | 148.00 | 7.5046 | 155.01 | 955.67 | 71.000 | 33.800 | 2.1006 | 1.4799e+08 | 141.57 |
| 19 | 3.5 mil black (top) | 170.00 | 7.9029 | 238.49 | 1105.0 | 84.800 | 30.000 | 2.8267 | 2.2362e+08 | 267.34 |
| 20 | 3.5 mil black (mid) | 170.00 | 7.6078 | 270.02 | 1023.3 | 84.800 | 31.300 | 2.7093 | 2.0497e+08 | 236.25 |
| 21 | 3.5 mil black (bot) | 170.00 | 5.8439 | 145.16 | 848.30 | 84.800 | 33.500 | 2.5313 | 1.6688e+08 | 170.00 |
| 22 | 3.5 mil black (top) re | 170.00 | 7.2127 | 174.18 | 1052.0 | 84.800 | 39.100 | 2.1688 | 1.9691e+08 | 287.23 |
| 23 | 3.5 mil black (mid) re | 170.00 | 5.5330 | 100.69 | 839.92 | 84.800 | 38.800 | 2.1856 | 1.5765e+08 | 182.31 |
| 24 | 3.5 mil black (bot) re | 170.00 | 7.2729 | 257.15 | 979.24 | 84.800 | 38.200 | 2.2199 | 1.8483e+08 | 245.63 |
| 25 | 1.5 mil white | 150.00 | 15.720 | 1285.9 | 1072.1 | 34.200 | 48.000 | 0.71250 | 32264e+07 | 21.500 |
| 26 | 1.7 mil white (top) | 100.00 | 10.982 | 604.66 | 493.54 | 41.600 | 39.600 | 1.0505 | 28407e+07 | 8.9463 |
| 27 | 1.7 mil white (mid) | 100.00 | 11.731 | 639.23 | 533.87 | 41.600 | 38.000 | 1.0947 | 3.1962e+07 | 10.494 |
| 28 | 1.7 mil white (bot) | 100.00 | 11.543 | 624.14 | 530.16 | 41.600 | 45.000 | 0.92444 | 2.6719e+07 | 10.151 |
| 29 | 2.5 mil white (mid) | 115.00 | 8.7830 | 503.19 | 506.86 | 49.300 | 44.000 | 1.1205 | 3.6739e+07 | 15.755 |
| 30 | 2.5 mil white (bot) | 115.00 | 13.938 | 1095.2 | 507.67 | 49.300 | 47.500 | 1.0379 | 3.4220e+07 | 15.739 |
| 31 | 2.5 mil white (top) | 127.00 | 10.966 | 931.26 | 461.42 | 49.300 | 47.000 | 1.0489 | 3.1428e+07 | 13.014 |
| 32 | 3.0 mil white (top) | 117.00 | 10.945 | 903.13 | 377.43 | 65.600 | 40.000 | 1.6400 | 4.8081e+07 | 19.401 |
| 33 | 3.0 mil white (mid) | 117.00 | 8.7849 | 634.56 | 393.27 | 65.600 | 42.000 | 1.5619 | 4.8697e+07 | 21.384 |
| 34 | 3.0 mil white (bot) | 117.00 | 8.9423 | 537.20 | 509.05 | 65.600 | 39.200 | 1.6735 | 65576e+07 | 35.050 |
| 35 | 1.5 mil green | 120.00 | 11.114 | 228.15 | 1105.5 | 44.600 | 43.800 | 1.0183 | 6.6145e+07 | 55.160 |
| 36 | 2.0 mil green (top) | 128.00 | 8.4436 | 199.56 | 881.22 | 50.500 | 45.600 | 1.1075 | 6.4734e+07 | 51.171 |
| 37 | 2.0 mil green (mid) | 128.00 | 7.6847 | 261.82 | 721.82 | 50.500 | 59.600 | 0.84732 | 3.9967e+07 | 33.042 |
| 38 | 2.0 mil green (bot) | 95.000 | 13.314 | 388.45 | 876.38 | 50.500 | 57.500 | 0.87826 | 5.0606e+07 | 49.115 |
| 39 | 2.5 mil green (top) | 130.00 | 5.2318 | 107.20 | 572.93 | 62.900 | 62.500 | 1.0064 | 4.7774e+07 | 41.503 |
| 40 | 2.5 mil green (mid) | 130.00 | 6.6506 | 313.98 | 550.60 | 62.900 | 59.700 | 1.0536 | 4.8054e+07 | 38.498 |
| 41 | 2.5 mil green (bot) | 130.00 | 6.4489 | 275.24 | 563.12 | 62.900 | 62.500 | 1.0064 | 4.6956e+07 | 40.093 |
| 42 | 3.0 mil green (top) | 117.00 | 6.0550 | 250.21 | 458.22 | 74.700 | 40.900 | 1.8264 | 7.0293e+07 | 40.539 |
| 43 | 3.0 mil green (mid) | 117.00 | 5.1929 | 173.81 | 433.76 | 74.700 | 45.500 | 1.6418 | 6.2959e+07 | 37.822 |
| 44 | 3.0 mil green (bot) | 117.00 | 6.2826 | 263.09 | 471.97 | 74.700 | 37.500 | 1.9920 | 7.5274e+07 | 41.328 |
| 45 | 3.5 mil green (top) | 138.00 | 6.4859 | 493.69 | 401.36 | 83.200 | 55.800 | 1.4910 | 6.1239e+07 | 46.004 |
| 46 | 3.5 mil green (mid) | 120.00 | 6.5981 | 367.95 | 423.82 | 83.200 | 51.000 | 1.6314 | 6.8272e+07 | 49.995 |
| 47 | 3.5 mil green (bot) | 132.00 | 5.3699 | 309.98 | 398.85 | 83.200 | 59.400 | 1.4007 | 5.8362e+07 | 46.045 |
| 48 | 1.5 mil red | 200.00 | 12.302 | 689.57 | 1770.8 | 43.200 | 46.000 | 0.93913 | 9.4292e+07 | 127.19 |
| 49 | 1.8 mil red-1 | 230.00 | 6.8388 | 437.03 | 1135.9 | 45.200 | 48.000 | 0.94167 | 6.3469e+07 | 59.969 |
| 50 | 1.8 mil red-2 (mid) | 205.00 | 11.847 | 790.95 | 1637.7 | 45.200 | 51.100 | 0.88454 | 85338e+07 | 123.17 |
| 51 | 1.8 mil red-2 (bot) | 205.00 | 9.7685 | 557.84 | 1444.7 | 45.200 | 52.000 | 0.86923 | 7.3780e+07 | 95.482 |
| 52 | 1.8 mil red-2 (across) | 230.00 | 6.0171 | 329.07 | 1054.9 | 45.200 | 48.000 | 0.94167 | 5.8942e+07 | 51.718 |
| 53 | 2.5 mil red (bot) | 190.00 | 9.4224 | 719.65 | 1070.6 | 51.200 | 48.200 | 1.0622 | 7.6662e+07 | 78.549 |
| 54 | 2.5 mil red (mid) | 190.00 | 7.9730 | 650.35 | 864.52 | 51.200 | 46.600 | 1.0987 | 6.3916e+07 | 51.312 |
| 55 | 2.5 mil red (top) | 190.00 | 6.5386 | 293.19 | 949.14 | 51.200 | 50.900 | 1.0059 | 6.4390e+07 | 61.429 |
| 56 | 3.0 mil red (top) | 185.00 | 10.259 | 912.85 | 985.07 | 75.600 | 48.700 | 1.5524 | 1.4005e+08 | 205.70 |
| 57 | 3.0 mil red (mid) | 185.00 | 9.1015 | 678.42 | 1005.4 | 75.600 | 50.400 | 1.5000 | 1.3992e+08 | 216.23 |
| 58 | 3.0 mil red (bot) | 185.00 | 5.3079 | 349.38 | 632.58 | 75.600 | 49.000 | 1.5429 | 8.9600e+07 | 84.974 |
| 59 | 3.5 mil red (top) | 220.00 | 6.4169 | 698.84 | 712.88 | 86.400 | 58.400 | 1.4795 | 1.1239e+08 | 162.83 |
| 60 | 3.5 mil red (mid) | 220.00 | 6.4276 | 706.84 | 707.23 | 86.400 | 48.400 | 1.7851 | 1.2409e+08 | 150.85 |
| 61 | 3.5 mil red (bot) | 220.00 | 5.3620 | 530.52 | 649.12 | 86.400 | 49.200 | 1.7561 | 1.1296e+08 | 127.91 |

TABLE 4

| Example | Sample | Ctri. En. | Slope | Intercept | 1/Rc | Thick | Radius | h/b | Pressure q | G | q2b/E | f (h/b) |
|---|---|---|---|---|---|---|---|---|---|---|---|---|
| 62 | red (top) re | 130 | 19.580 | 1896.9 | 648.50 | 47.73 | 51.5 | 0.927 | 4.92e+07 | 40.1 | 41.560 | 1.0372 |
| 63 | red (mid) | 140 | 12.865 | 1179.2 | 621.07 | 47.73 | 52.0 | 0.918 | 4.68e+07 | 37.0 | 37.979 | 1.0274 |
| 64 | red (bot) | 140 | 11.829 | 1108.8 | 547.26 | 47.73 | 53.1 | 0.899 | 4.05e+07 | 28.8 | 28.992 | 1.0061 |
| 65 | red (top) | 130 | 16.011 | 1495.4 | 586.03 | 47.73 | 45.5 | 1.05 | 4.89e+07 | 31.3 | 36.228 | 1.1573 |
|  | AVERAGE: 62–65 |  |  |  |  |  |  |  |  | 34.3 |  |  |
| 66 | burgundy (top) | 110 | 6.0794 | 335.94 | 332.79 | 46.25 | 49.9 | 0.927 | 2.45e+07 | 9.60 | 9.9582 | 1.0372 |
| 67 | burgundy (mid) | 106 | 8.4099 | 389.36 | 502.09 | 46.25 | 59.1 | 0.783 | 3.17e+07 | 23.0 | 19.759 | 0.86072 |
| 68 | burgundy (bot) | 110 | 5.9845 | 274.93 | 383.36 | 46.25 | 52.2 | 0.886 | 2.71e+07 | 12.9 | 12.811 | 0.99130 |
|  | AVERAGE: 66–68 |  |  |  |  |  |  |  |  | 15.2 |  |  |
| 69 | burgundy (top) | 110 | 9.4016 | 704.51 | 329.67 | 49.61 | 55.4 | 0.895 | 2.53e+07 | 11.8 | 11.782 | 1.0022 |
| 70 | burgundy (mid) | 115 | 9.7166 | 839.43 | 277.98 | 49.61 | 55.3 | 0.897 | 2.13e+07 | 8.35 | 8.3877 | 1.0041 |
| 71 | burgundy (bot) | 115 | 6.0287 | 411.35 | 281.95 | 49.61 | 51.2 | 0.969 | 2.30e+07 | 8.38 | 9.0607 | 1.0814 |
| 72 | burg. (top) re | 115 | 9.4010 | 704.51 | 376.60 | 49.61 | 59.0 | 0.841 | 2.73e+07 | 15.6 | 14.644 | 0.93685 |
|  | AVERAGE: 69–72 |  |  |  |  |  |  |  |  | 11.0 |  |  |
| 73 | burgundy (top) | 112 | 10.697 | 753.98 | 444.08 | 48.22 | 52.1 | 0.926 | 3.40e+07 | 19.4 | 20.077 | 1.0358 |
| 74 | burgundy (mid) | 120 | 9.7831 | 717.34 | 456.63 | 48.22 | 52.7 | 0.915 | 3.46e+07 | 20.6 | 21.068 | 1.0242 |
| 75 | burgundy (bot) | 119 | 7.9193 | 445.18 | 497.22 | 48.22 | 50.5 | 0.955 | 3.90e+07 | 24.0 | 25.659 | 1.0670 |
|  | AVERAGE: 73–75 |  |  |  |  |  |  |  |  | 21.3 |  |  |
| 76 | red (top) re | 135 | 10.843 | 1009.7 | 454.11 | 50.19 | 63.3 | 0.793 | 3.15e+07 | 23.9 | 20.919 | 0.87469 |
| 77 | red (mid) | 134 | 14.012 | 1324.5 | 553.11 | 50.19 | 60.6 | 0.828 | 4.00e+07 | 35.1 | 32.290 | 0.92091 |

TABLE 4-continued

| Example | Sample | Ctri. En. | Slope | Intercept | l/Rc | Thick | Radius | h/b | Pressure q | G | q2b/E | f (h/b) |
|---|---|---|---|---|---|---|---|---|---|---|---|---|
| 78 | red (bot) | 132 | 12.687 | 1069.2 | 605.48 | 50.19 | 57.7 | 0.870 | 4.58e+07 | 41.4 | 40.278 | 0.97226 |
| 79 | red (top) | 130 | 9.0967 | 795.80 | 386.77 | 50.19 | 56.0 | 0.896 | 3.00e+07 | 16.8 | 16.803 | 1.0031 |
| | AVERAGE: 76–79 | | | | | | | | | 29.3 | | |
| 80 | burgundy (top) | 119 | 6.9692 | 317.63 | 457.70 | 38.87 | 51.3 | 0.758 | 2.35e+07 | 11.4 | 9.4340 | 0.82621 |
| 81 | burgundy (mid) | 125 | 7.1467 | 487.47 | 405.87 | 38.87 | 53.0 | 0.733 | 2.0le+07 | 9.05 | 7.1622 | 0.79133 |
| 82 | burgundy (bot) | 119 | 9.8352 | 672.72 | 497.67 | 38.87 | 53.2 | 0.731 | 2.46e+07 | 13.6 | 10.724 | 0.78731 |
| | AVERAGE: 80–82 | | | | | | | | | 11.4 | | |
| 83 | burgundy (top) | 116 | 8.6004 | 534.04 | 463.61 | 49.2 | 54.9 | 0.896 | 3.53e+07 | 22.7 | 22.740 | 1.0030 |
| 84 | burgundy (mid) r | 114 | 8.9910 | 607.59 | 417.38 | 49.2 | 60.9 | 0.808 | 2.89e+07 | 18.9 | 16.941 | 0.89460 |
| 85 | burgundy (bot) | 121 | 7.9804 | 481.16 | 484.47 | 49.2 | 52.2 | 0.943 | 3.84e+07 | 24.4 | 25.674 | 1.0540 |
| 86 | burgundy (mid) | 107 | 8.9910 | 607.59 | 354.45 | 49.2 | 44.6 | 1.10 | 3.15e+07 | 12.3 | 14.785 | 1.2030 |
| | AVERAGE: 83–86 | | | | | | | | | 19.6 | | |
| 87 | burgundy (top) | 117 | 8.1543 | 401.88 | 552.17 | 44.28 | 58.3 | 0.760 | 3.24e+07 | 24.6 | 20.349 | 0.82877 |
| 88 | burgundy (mid) | 125 | 8.1373 | 440.41 | 576.75 | 44.28 | 60.5 | 0.732 | 3.25e+07 | 27.0 | 21.333 | 0.78915 |
| 89 | burg. (bot) re | 122 | 11.115 | 687.54 | 668.49 | 44.28 | 62.3 | 0.711 | 3.65e+07 | 36.6 | 27.715 | 0.75785 |
| 90 | burgundy (bot) | 122 | 11.527 | 725.14 | 681.15 | 44.28 | 52.9 | 0.837 | 4.39e+07 | 36.4 | 33.935 | 0.93209 |
| | AVERAGE: 87–90 | | | | | | | | | 31.1 | | |
| 91 | red (top) | 138 | 13.877 | 1422.5 | 492.53 | 46.25 | 56.5 | 0.819 | 3.24e+07 | 21.8 | 19.830 | 0.90855 |
| 92 | red (mid) | 135 | 10.813 | 905.66 | 554.09 | 46.25 | 59.4 | 0.779 | 3.48e+07 | 28.0 | 23.945 | 0.85532 |
| 93 | red (bot) | 144 | 10.277 | 943.29 | 536.60 | 46.25 | 55.2 | 0.838 | 3.61e+07 | 25.7 | 24.017 | 0.93311 |
| | AVERAGE: 91–93 | | | | | | | | | 25.2 | | |
| 94 | burgundy (top) | 120 | 15.584 | 1368.2 | 501.88 | 41.82 | 52.1 | 0.803 | 2.93e+07 | 16.8 | 14.953 | 0.88775 |
| 95 | burgundy (mid) | 126 | 7.2048 | 393.13 | 514.67 | 41.82 | 50.3 | 0.831 | 3.11e+07 | 17.5 | 16.228 | 0.92497 |
| 96 | burgundy (bot) | 130 | 9.2576 | 743.59 | 459.90 | 41.82 | 53.4 | 0.783 | 2.62e+07 | 14.2 | 12.265 | 0.86150 |
| | AVERAGE: 94–96 | | | | | | | | | 16.2 | | |
| 97 | red (top) | 140 | 10.320 | 872.43 | 572.37 | 41.82 | 57.2 | 0.731 | 3.04e+07 | 22.4 | 17.678 | 0.78801 |
| 98 | red (mid) | 141 | 10.858 | 976.71 | 554.27 | 41.82 | 53.7 | 0.779 | 3.15e+07 | 20.7 | 17.717 | 0.85552 |
| 99 | red (bot) | 141 | 9.7655 | 792.73 | 584.21 | 41.82 | 56.2 | 0.744 | 3.17e+07 | 23.3 | 18.777 | 0.80687 |
| | AVERAGE: 97–99 | | | | | | | | | 22.1 | | |
| 100 | burgundy (top) | 126 | 7.6230 | 405.00 | 555.50 | 44.77 | 55.0 | 0.814 | 3.52e+07 | 25.2 | 22.765 | 0.90260 |
| 101 | burgundy (mid) | 134 | 6.5211 | 387.03 | 486.80 | 44.77 | 53.3 | 0.840 | 3.18e+07 | 19.2 | 17.967 | 0.93574 |
| 102 | burgundy (bot) | 135 | 7.5999 | 475.90 | 550.09 | 44.77 | 55.1 | 0.813 | 3.48e+07 | 24.7 | 22.288 | 0.90068 |
| | AVERAGE: 100–102 | | | | | | | | | 23.1 | | |
| 103 | red (top) | 143 | 10.388 | 971.78 | 513.70 | 47.73 | 57.0 | 0.837 | 3.57e+07 | 25.9 | 24.181 | 0.93249 |
| 104 | red (mid) | 146 | 10.555 | 1049.8 | 491.23 | 47.73 | 55.6 | 0.858 | 3.49e+07 | 23.5 | 22.567 | 0.95854 |
| 105 | red (bot) | 146 | 9.0442 | 809.48 | 510.97 | 47.73 | 53.5 | 0.892 | 3.75e+07 | 25.2 | 25.140 | 0.99840 |
| | AVERAGE: 103–105 | | | | | | | | | 24.9 | | |
| 106 | burg. (top) re | 141 | 6.1521 | 463.24 | 404.21 | 44.28 | 56.6 | 0.782 | 2.44e+07 | 13.1 | 11.235 | 0.86039 |
| 107 | burgundy (mid) | 135 | 5.9048 | 312.11 | 485.04 | 44.28 | 56.2 | 0.788 | 2.95e+07 | 18.8 | 16.290 | 0.86796 |
| 108 | burgundy (bot) | 135 | 8.5351 | 525.81 | 626.43 | 44.28 | 55.2 | 0.802 | 3.88e+07 | 31.2 | 27.637 | 0.88707 |
| 109 | burgundy (top) | 135 | 6.0066 | 453.54 | 357.36 | 44.28 | 49.1 | 0.902 | 2.46e+07 | 9.80 | 9.8933 | 1.0095 |
| | AVERAGE: 106–109 | | | | | | | | | 18.2 | | |
| 110 | red (top) re | 161 | 7.1780 | 633.63 | 522.03 | 48.22 | 64.0 | 0.753 | 3.30e+07 | 28.4 | 23.290 | 0.82017 |
| 111 | red (mid) re | 160 | 7.4750 | 772.12 | 423.88 | 48.22 | 60.9 | 0.792 | 2.82e+07 | 18.5 | 16.142 | 0.87321 |
| 112 | red (bot) re | 155 | 15.685 | 1773.7 | 657.48 | 48.22 | 58.6 | 0.823 | 4.54e+07 | 44.0 | 40.233 | 0.91407 |
| 113 | red (top) | 152 | 10.827 | 1106.1 | 539.60 | 48.22 | 64.7 | 0.745 | 3.38e+07 | 30.4 | 24.598 | 0.80853 |
| 114 | red (mid) | 160 | 10.160 | 1175.9 | 449.70 | 48.22 | 60.9 | 0.792 | 2.99e+07 | 20.8 | 18.169 | 0.87321 |
| 115 | red (bot) | 145 | 13.696 | 1505.3 | 480.62 | 48.22 | 51.4 | 0.938 | 3.72e+07 | 22.6 | 23.720 | 1.0494 |
| | AVERAGE: 110–115 | | | | | | | | | 27.5 | | |
| 116 | red (top) unexp | 171 | 9.9457 | 853.44 | 847.27 | 53.3 | 71.6 | 0.744 | 5.85e+07 | 101 | 81.800 | 0.80728 |
| 117 | red (mid) unexp | 171 | 7.4249 | 493.42 | 776.24 | 53.3 | 73.2 | 0.728 | 5.24e+07 | 85.5 | 67.007 | 0.78365 |
| 118 | red (bot) unexp | 167 | 8.9938 | 791.18 | 710.78 | 53.3 | 71.8 | 0.742 | 4.90e+07 | 71.4 | 57.394 | 0.80430 |
| | AVERAGE: 116–118 | | | | | | | | | 86.1 | | |
| 119 | red (top) unexp | 133 | 12.195 | 902.58 | 719.41 | 49.5 | 60.5 | 0.818 | 5.07e+07 | 57.1 | 52.845 | 0.90803 |
| 120 | red (mid) unexp | 139 | 11.032 | 960.64 | 572.81 | 49.5 | 61.1 | 0.810 | 4.00e+07 | 36.3 | 32.578 | 0.89757 |
| 121 | red (bot) unexp | 144 | 9.3353 | 831.40 | 512.88 | 49.5 | 63.9 | 0.775 | 3.43e+07 | 29.4 | 25.024 | 0.84986 |
| | AVERAGE: 119–121 | | | | | | | | | 40.9 | | |
| 122 | burg. (top) unexp | 141 | 6.9389 | 484.11 | 494.27 | 53.1 | 62.4 | 0.851 | 3.88e+07 | 32.9 | 31.239 | 0.94938 |
| 123 | burg. (mid) unexp | 137 | 6.8269 | 442.27 | 493.02 | 53.1 | 63.8 | 0.832 | 3.79e+07 | 32.9 | 30.509 | 0.92608 |
| 124 | burg. (bot) unexp | 140 | 7.2432 | 491.27 | 522.78 | 53.1 | 62.8 | 0.846 | 4.08e+07 | 36.9 | 34.763 | 0.94269 |
| | AVERAGE: 122–124 | | | | | | | | | 34.2 | | |
| 125 | burg. (top) unexp | 141 | 5.9768 | 529.87 | 312.86 | 54.6 | 66.8 | 0.817 | 2.43e+07 | 14.5 | 13.147 | 0.90697 |
| 126 | burg. (mid) unexp | 142 | 7.8065 | 713.47 | 395.05 | 54.6 | 67.9 | 0.804 | 3.02e+07 | 23.2 | 20.654 | 0.88965 |
| 127 | burg. (bot) unexp | 143 | 9.5188 | 938.78 | 422.41 | 54.6 | 68.4 | 0.798 | 3.21e+07 | 26.6 | 23.452 | 0.88185 |
| | AVERAGE: 125–127 | | | | | | | | | 21.4 | | |

TABLE 5

| Example | Sample | C.E. | Slope | Intercept | 1/RC | Thick | Radius | hlb | Pressure q | G | q2b/E | f (h/b) |
|---|---|---|---|---|---|---|---|---|---|---|---|---|
| 128 | 768C/GEN3 (top) | 132 | 9.4705 | 480.51 | 769.60 | 54.25 | 71.9 | 0.755 | 3.96e+07 | 78.7 | 37.643 | 0.47861 |
| 129 | 768C/GEN3 (mid) | 142 | 9.0385 | 352.28 | 931.19 | 54.25 | 73.9 | 0.734 | 4.63e+07 | 116 | 52.717 | 0.45586 |
| 130 | 768C/GEN3 (bot) | 140 | 9.6854 | 313.00 | 1043.0 | 54.25 | 80.3 | 0.676 | 4.63e+07 | 147 | 57.345 | 0.39030 |
| | AVERAGE: 128–130 | | | | | | | | | 114 | | |

TABLE 5-continued

| Example | Sample | C.E. | Slope | Intercept | 1/RC | Thick | Radius | h1b | Pressure q | G | q2b/E | f (h/b) |
|---|---|---|---|---|---|---|---|---|---|---|---|---|
| 131 | 768C/CRO/30 m @ 240 (top) | 97.0 | 23.287 | 426.51 | 1832.3 | 41.5 | 79.5 | 0.522 | 4.23e+07 | 211 | 47.425 | 0.22483 |
| 132 | 768C/CRO/30 m @ 240 (mid) 1 | 42 | 20.817 | 344.41 | 2611.6 | 41.5 | 96.5 | 0.430 | 4.38e+07 | 440 | 61.778 | 0.14026 |
| 133 | 768C/CRO/30 m @ 240 (bot) | 96.0 | 25.012 | 486.06 | 1915.1 | 41.5 | 80.1 | 0.518 | 4.37e+07 | 231 | 50.964 | 0.22093 |
| | AVERAGE: 131–133 | | | | | | | | | 294 | | |
| 134 | 768C/CRO/30 m @ 285 (top) | 110 | 16.958 | 467.72 | 1397.7 | 38.25 | 55.0 | 0.695 | 4.55e+07 | 92.1 | 37.989 | 0.41258 |
| 135 | 768C/CRO/30 m @ 285 (mid) | 120 | 16.817 | 367.99 | 1650.0 | 38.25 | 56.9 | 0.672 | 5.13e+07 | 129 | 49.862 | 0.38654 |
| 136 | 768C/CRO/30 m @ 285 (bot) | 118 | 18.494 | 529.58 | 1652.7 | 38.25 | 58.6 | 0.653 | 4.93e+07 | 130 | 47.412 | 0.36474 |
| | AVERAGE: 134–136 | | | | | | | | | 117 | | |
| 137 | 768C/CRO/60 m @ 380 (top) | 80.0 | 21.975 | 471.67 | 1286.3 | 36.25 | 50.4 | 0.719 | 4.16e+07 | 66.0 | 29.010 | 0.43925 |
| 138 | 768C/CRO/60 m @ 380 (mid) | 84.0 | 23.418 | 431.42 | 1535.7 | 36.25 | 60.1 | 0.603 | 3.87e+07 | 96.7 | 29.968 | 0.31001 |
| 139 | 768C/CRO/60 m @ 380 (bot) | 82.0 | 19.526 | 391.97 | 1209.2 | 36.25 | 60.0 | 0.604 | 3.05e+07 | 59.9 | 18.640 | 0.31111 |
| | AVERAGE: 137–139 | | | | | | | | | 74.2 | | |
| 140 | UBP/CRO/60 m @ 380 (top) | 125 | 20.215 | 530.18 | 1996.7 | 44 | 60.8 | 0.724 | 7.89e+07 | 284 | 126.29 | 0.44422 |
| 141 | UBP/CRO/60 m @ 380 (mid) | 110 | 19.489 | 480.69 | 1663.1 | 44 | 54.7 | 0.804 | 7.53e+07 | 194 | 103.47 | 0.53342 |
| 142 | UBP/CRO/60 m @ 380 (bot) | 130 | 18.291 | 446.78 | 1931.1 | 44 | 62.3 | 0.706 | 7.39e+07 | 267 | 113.36 | 0.42470 |
| 143 | UBP/CRO/30 m @ 285 (top) | 105 | 24.656 | 994.60 | 1594.3 | 45.5 | 61.4 | 0.741 | 6.73e+07 | 200 | 92.581 | 0.46361 |
| 144 | UBP/CRO/30 m @ 285 (mid) | 123 | 19.627 | 449.62 | 1964.5 | 45.5 | 63.6 | 0.715 | 7.91e+07 | 305 | 132.60 | 0.43495 |
| 145 | UBP/CRO/30 m @ 285 (bot) | 117 | 17.215 | 408.84 | 1605.3 | 45.5 | 60.6 | 0.751 | 6.89e+07 | 202 | 95.876 | 0.47450 |
| | AVERAGE: 140–145 | | | | | | | | | 235 | | |
| 146 | UBP/CRO/30 m @ 240 (top) | 168 | 12.415 | −58.104 | 2143.8 | 39.5 | 64.5 | 0.612 | 6.02e+07 | 243 | 77.846 | 0.32011 |
| 147 | UBP/CRO/30 m @ 240 (mid) | 168 | 21.636 | 545.18 | 3089.7 | 39.5 | 64.5 | 0.612 | 8.67e+07 | 505 | 161.69 | 0.32011 |
| 148 | UBP/CRO/30 m @ 240 (bot) | 168 | 18.965 | 453.48 | 2732.6 | 39.5 | 64.5 | 0.612 | 7.67e+07 | 395 | 126.48 | 0.32011 |
| | AVERAGE: 146–148 | | | | | | | | | 381 | | |

TABLE 6

| Example | Sample/Panel No. | C.E. | Slope | Intercept | 1/RC | Thick | Radius | h/b | Pressure q | G | q2b/E | f (h/b) |
|---|---|---|---|---|---|---|---|---|---|---|---|---|
| 149 | bfc-24 grey (top) exp | 202 | 6.8751 | 365.25 | 1023.5 | 41.3 | 59.7 | 0.692 | 3.57e+07 | 62.2 | 25.410 | 0.40847 |
| 150 | bfc-24 grey (mid) exp | 204 | 7.3897 | 542.21 | 965.29 | 41.3 | 63.3 | 0.652 | 3.11e+07 | 55.8 | 20.343 | 0.36443 |
| 151 | bfc-24 grey (bot) exp | 175 | 8.9302 | 707.66 | 855.12 | 41.3 | 59.6 | 0.740 | 3.27e+07 | 43.0 | 19.880 | 0.46261 |
| | AVERAGE: 149–151 | 194 | | | 947.98 | | 59.6 | 0.695 | | 53.6 | | |
| 152 | bfc-13 red (top) exp | 226 | 11.529 | 892.91 | 1712.6 | 34.5 | 48.2 | 0.716 | 5.23e+07 | 101 | 43.972 | 0.43535 |
| 153 | bfc-13 red (mid) exp | 280 | 6.4172 | 158.28 | 1638.5 | 34.5 | 40.2 | 0.858 | 6.29e+07 | 89.8 | 53.056 | 0.59090 |
| 154 | bfc-13 red (bot) exp | 269 | 7.8254 | 553.83 | 1551.2 | 34.5 | 45.1 | 0.765 | 5.17e+07 | 82.0 | 40.198 | 0.49018 |
| | AVERAGE: 152–154 | 258 | | | 1634.1 | | 44.5 | 0.780 | | 92.7 | | |
| 155 | bfc-9 red (top) exp | 248 | 7.4745 | 1256.1 | 597.58 | 70.3 | 48.9 | 1.44 | 7.52e+07 | 88.5 | 92.212 | 1.0420 |
| 156 | bfc-9 red (mid) exp | 243 | 8.8027 | 1555.9 | 583.16 | 70.3 | 45.8 | 1.53 | 7.66e+07 | 82.1 | 89.499 | 1.0905 |
| 157 | bfc-9 red (bot) exp | 248 | 6.3219 | 1033.2 | 534.63 | 70.3 | 47.5 | 1.48 | 6.86e+07 | 70.0 | 74.502 | 1.0638 |
| | AVERAGE: 155–157 | 246 | | | 571.79 | | 47.4 | 1.48 | | 80.2 | | |
| 158 | RE-bfc-4 red (top) exp | 207 | 4.4611 | 390.96 | 532.49 | 57.8 | 48.7 | 1.19 | 4.76e+07 | 41.6 | 36.798 | 0.88476 |
| 159 | RE-bfc-4 red (mid) exp | 206 | 4.2069 | 239.17 | 627.45 | 57.8 | 48.8 | 1.18 | 5.60e+07 | 57.8 | 51.018 | 0.88297 |
| 160 | RE-bfc-4 red (bot) exp | 195 | 4.5589 | 474.73 | 414.26 | 57.8 | 45.8 | 1.26 | 3.90e+07 | 24.7 | 23.175 | 0.93734 |
| | AVERAGE: 158–160 | 203 | | | 524.73 | | 47.8 | 1.21 | | 41.4 | | |
| 161 | bfc-10 red (top) exp | 297 | 6.3897 | 686.92 | 1210.8 | 56 | 59.1 | 0.948 | 8.44e+07 | 206 | 140.29 | 0.68114 |
| 162 | bfc-10 red (mid) exp | 311 | 5.3260 | 557.57 | 1098.8 | 56 | 54.0 | 1.04 | 8.41e+07 | 167 | 127.20 | 0.76395 |
| 163 | bfc-10 red (bot) exp | 311 | 4.7220 | 358.89 | 1109.7 | 56 | 59.0 | 0.949 | 7.75e+07 | 173 | 118.06 | 0.68269 |
| | AVERAGE: 161–163 | 306 | | | 1139.8 | | 57.4 | 0.978 | | 182 | | |
| 164 | bfc-6 red (top) exp re | 216 | 5.1459 | 529.76 | 581.75 | 64.8 | 45.4 | 1.43 | 6.72e+07 | 65.9 | 68.270 | 1.0364 |
| 165 | bfc-6 red (mid) exp re | 222 | 4.4498 | 424.21 | 563.65 | 64.8 | 46.7 | 1.39 | 6.38e+07 | 62.5 | 63.392 | 1.0145 |
| 166 | bfc-6 red (bot) exp re | 207 | 5.1091 | 449.80 | 607.78 | 64.8 | 43.5 | 1.49 | 7.22e+07 | 70.7 | 75.551 | 1.0687 |
| | AVERAGE: 164–166 | 215 | | | 584.40 | | 45.2 | 1.43 | | 66.4 | | |
| 167 | bfc-7 red (top) exp | 215 | 6.6144 | 401.52 | 1020.6 | 53 | 55.4 | 0.957 | 6.80e+07 | 124 | 85.427 | 0.68995 |
| 168 | bfc-7 red (mid) exp | 225 | 5.6660 | 314.01 | 960.84 | 53 | 54.5 | 0.972 | 6.52e+07 | 109 | 77.122 | 0.70500 |
| 169 | bfc-7 red (bot) exp | 213 | 7.6374 | 603.62 | 1023.1 | 53 | 53.0 | 1.00 | 7.14e+07 | 123 | 90.116 | 0.73064 |
| | AVERAGE: 167–169 | 218 | | | loo1.5 | | 54.3 | 0.976 | | 119 | | |
| 170 | bfa-14 grey (top) unexp | 286 | 3.0065 | 150.79 | 709.07 | 50.5 | 106 | 0.476 | 1.72e+07 | 57.5 | i0.434 | 0.18091 |
| 171 | bfa-14 grey (mid) unexp | 285 | 2.6934 | 64.894 | 702.72 | 50.5 | 105 | 0.481 | 1.73e+07 | 56.6 | 10.472 | 0.18512 |
| 172 | bfa-14 grey (bot) unexp | 286 | 2.3738 | 41.644 | 637.26 | 50.5 | 109 | 0.463 | 1.47e+07 | 46.8 | 7.9026 | 0.16897 |
| | AVERAGE: 170–172 | | | | | | | | | 53.7 | | |
| 173 | bfa-9 red (top) unexp | 301 | 2.7276 | 182.98 | 638.03 | 84.3 | 62.6 | 1.35 | 9.20e+07 | 178 | 176.50 | 0.99074 |
| 174 | bfa-9 red (mid) unexp | 301 | 3.7766 | 493.14 | 643.62 | 84.3 | 57.3 | 1.47 | 9.86e+07 | 175 | 185.85 | 1.0594 |
| 175 | bfa-9 red (bot) unexp | 305 | 3.6942 | 360.26 | 766.47 | 84.3 | 62.4 | 1.35 | 1.11e+08 | 257 | 255.10 | 0.99331 |
| | AVERAGE: 173–175 | | | | | | | | | 203 | | |
| 176 | bfa-4 red (top) unexp | 187 | 4.6316 | 347.87 | 518.24 | 71.3 | 58.8 | 1.21 | 5.82e+07 | 73.5 | 66.397 | 0.90334 |
| 177 | bfa-4 red (mid) unexp | 187 | 5.0685 | 405.32 | 542.49 | 71.3 | 55.9 | 1.28 | 6.35+07 | 79.3 | 75.064 | 0.94625 |
| 178 | bfa-4 red (bot) unexp | 185 | 5.0717 | 442.41 | 495.85 | 71.3 | 59.6 | 1.20 | 5.51e+07 | 67.5 | 60.229 | 0.89166 |
| | AVERAGE: 176–178 | | | | | | | | | 73.5 | | |
| 179 | bfa-10 red (top) unexp | 356 | 5.2891 | 542.65 | 1340.3 | 44.3 | 65.1 | 0.680 | 4.91e+07 | 132 | 52.234 | 0.39580 |
| 180 | bfa-10 red (mid) unexp | 350 | 5.8138 | 706.12 | 1328.7 | 44.3 | 62.6 | 0.708 | 5.13e+07 | 129 | 54.961 | 0.42628 |
| 181 | bfa-10 red (bot) unexp | 355 | 5.5970 | 661.43 | 1325.5 | 44.3 | 62.0 | 0.715 | 5.19e+07 | 128 | 55.599 | 0.43395 |
| | AVERAGE: 179–181 | | | | | | | | | 130 | | |
| 181 | bfa-6 red (top) unexp | 199 | 4.6034 | 485.43 | 430.65 | 72 | 52.4 | 1.37 | 5.38e+07 | 50.2 | 50.553 | 1.0068 |
| 183 | bfa-6 red (mid) unexp | 190 | 6.1590 | 705.21 | 465.00 | 72 | 52.1 | 1.38 | 5.83e+07 | 58.4 | 59.084 | 1.0113 |

TABLE 6-continued

| Example | Sample/Panel No. | C.E. | Slope | Intercept | 1/RC | Thick | Radius | h/b | Pressure q | G | q2b/E | f (h/b) |
|---|---|---|---|---|---|---|---|---|---|---|---|---|
| 184 | bfa-6 red (bot) unexp | 195 | 5.9467 | 676.85 | 482.76 | 72 | 54.7 | 1.32 | 5.84e+07 | 64.0 | 62.259 | 0.97225 |
|  | AVERAUE: 182–184 |  |  |  |  |  |  |  |  | 57.6 |  |  |
| 185 | bfa-7 red (top) unexp | 295 | 4.4977 | 264.23 | 1062.6 | 65.3 | 65.6 | 0.995 | 9.10e+07 | 249 | 180.91 | 0.72643 |
| 186 | bfa-7 red (mid) unexp | 311 | 3.6461 | 306.22 | 827.72 | 65.3 | 61.7 | 1.06 | 7.53e+07 | 149 | 116.69 | 0.78249 |
| 187 | bfa-7 red (bot) unexp | 295 | 5.4690 | 575.81 | 1037.5 | 65.3 | 54.3 | 1.20 | 1.06e+08 | 227 | 203.30 | 0.89618 |
|  | AVERAGE: 185–187 |  |  |  |  |  |  |  |  | 208 |  |  |

TABLE 7

| Example | Sample | C.E. | Slope | Intercept | 1/Rc | Thick | Radius | h/b | Pressure q | G | q2b/E | f (h/b) |
|---|---|---|---|---|---|---|---|---|---|---|---|---|
| 188 | #1, 17 m @ 330, gas grey (top) | 178 | 7.2351 | 152.29 | 1135.6 | 42.7 | 100 | 0.427 | 1.94e+07 | 90.8 | 12.507 | 0.13775 |
| 189 | #1, 17 m @ 330, gas grey (mid) | 175 | 7.7158 | 128.05 | 1222.2 | 42.7 | 97.7 | 0.437 | 2.17e+07 | 105 | 15.319 | 0.14611 |
| 190 | #1, 17 m @ 330, gas grey (bot) | 170 | 8.3051 | 187.78 | 1224.1 | 42.7 | 95.4 | 0.448 | 2.26e+07 | 105 | 16.259 | 0.15511 |
|  | AVERAGE: 188–190 |  |  |  |  |  |  |  |  | 100 |  |  |
| 191 | #1, 17 m @ 330, electric grey (top) | 97.0 | 16.782 | 830.64 | 797.21 | 38.4 | 69.4 | 0.553 | 1.87e+07 | 31.4 | 8.0546 | 0.25680 |
| 192 | #1, 17 m @ 330 electric grey (mid) | 94.0 | 13.005 | 437.87 | 784.60 | 38.4 | 69.5 | 0.553 | 1.83e+07 | 30.4 | 7.7782 | 0.25598 |
| 193 | #1, 17 m @ 330,electric grey (bot) | 89.0 | 19.080 | 774.01 | 924.11 | 38.4 | 62.0 | 0.619 | 2.56e+07 | 41.4 | 13.583 | 0.32774 |
|  | AVERAGE: 191–193 |  |  |  |  |  |  |  |  | 34.3 |  |  |
| 194 | #1, 17 m @ 360, gas grey (top) | 120 | 12.724 | 463.58 | 1063.3 | 42.7 | 76.6 | 0.557 | 2.80e+07 | 76.6 | 20.010 | 0.26111 |
| 195 | #1, 17 m @ 360, gas grey (mid) | 140 | 11.209 | 369.56 | 1199.8 | 42.7 | 85.8 | 0.498 | 2.64e+07 | 99.2 | 19.933 | 0.20095 |
| 196 | #1, 17 m @ 360, gas grey (bot) | 121 | 12.827 | 318.82 | 1233.2 | 42.7 | 72.1 | 0.592 | 3.56e+07 | 102 | 30.462 | 0.29815 |
|  | AVERAGE: 194–196 |  |  |  |  |  |  |  |  | 92.7 |  |  |
| 197 | #1, 17 m @ 360 electric grey (top) | 105 | 12.741 | 353.16 | 984.65 | 42.2 | 69.9 | 0.604 | .2.89e+07 | 62.7 | 19.472 | 0.31062 |
| 198 | #1, 17 m @ 360 electric grey (mid) | 84.0 | 16.981 | 660.50 | 765.90 | 42.2 | 63.1 | 0.669 | 2.61e+07 | 37.4 | 14.294 | 0.38268 |
| 199 | #1, 17 m @ 360,electric grey (bot) | 110 | 13.249 | 332.47 | 1124.9 | 42.2 | 69.2 | 0.610 | 3.35e+07 | 81.7 | 25.922 | 0.31729 |
|  | AVERAGE: 197–199 |  |  |  |  |  |  |  |  | 60.6 |  |  |
| 200 | #1, 17 m @ 390, gas grey (top) | 131 | 11.255 | 164.22 | 1310.2 | 39.1 | 75.9 | 0.515 | 2.79e+07 | 90.4 | 19.702 | 0.21800 |
| 201 | #1, 17 m @ 390, gas grey (mid) | 150 | 9.0766 | 130.40 | 1231.1 | 39.1 | 74.4. | 0.526 | 2.71e+07 | 79.6 | 18.168 | 0.22836 |
| 202 | #1, 17 m @ 390, gas grey (bot) | 112 | 12.203 | 229.36 | 1149.6 | 39.1 | 74.8 | 0.523 | 2.51e+07 | 69.4 | 15.659 | 0.22554 |
|  | AVERAGE: 200–202 |  |  |  |  |  |  |  |  | 79.8 |  |  |
| 203 | #1, 17 m @ 390, electric grey (top) | 82.0 | 13.537 | 475.03 | 635.00 | 43.4 | 67.5 | 0.643 | 2.10e+07 | 28.1 | 9.9417 | 0.35386 |
| 204 | #1, 17 m @ 390, electric grey (mid) | 81.0 | 11.493 | 295.43 | 635.50 | 43.4 | 63.9 | 0.679 | 2.27e+07 | 27.9 | 11.005 | 0.39433 |
| 205 | #1, 17 m @ 390, electric grey (bot) | 80.0 | 15.948 | 519.85 | 755.99 | 43.4 | 65.7 | 0.661 | 2.60e+07 | 39.7 | 14.813 | 0.37350 |
|  | AVERAGE: 203–205 |  |  |  |  |  |  |  |  | 31.9 |  |  |
| 206 | #1, 30 m @ 390, gas grey (top) | 135 | 10.072 | 211.65 | 1148:1 | 47.8 | 76.4 | 0.626 | 4.02e+07 | 123 | 41.232 | 0.33469 |
| 207 | #1, 30 m @ 390, gas grey (mid) | 137 | 9.3942 | 109.42 | 1177.6 | 47.8 | 75.0 | 0.637 | 4.24e+07 | 129 | 44.930 | 0.34761 |
| 208 | #1, 30 m @ 390, gas grey (bot) | 135 | 12.515 | 301.23 | 1388.3 | 47.8 | 75.9 | 0.630 | 4.91e+07 | 180 | 61.053 | 0.33924 |
|  | AVERAGE: 206–208 |  |  |  |  |  |  |  |  | 144 |  |  |
| 209 | #1, 30 m @ 390, electric grey (top) | 96.0 | 12.826 | 405.74 | 825.56 | 39.4 | 65.6 | 0.601 | 2.25e+07 | 35.9 | 11.027 | 0.30724 |
| 210 | #1, 30 m @ 390 electric grey (mid) | 98.0 | 12.634 | 313.50 | 924.68 | 39.4 | 68.1 | 0.579 | 2.38e+07 | 45.3 | 12.835 | 0.28346 |
| 211 | #1, 30 m @ 390, electric grey (bot) | 96.0 | 17.743 | 551.37 | 1152.0 | 39.4 | 67.9 | 0.580 | 2.98e+07 | 70.2 | 20.039 | 0.28528 |
|  | AVERAGE: 209–211 |  |  |  |  |  |  |  |  | 50.5 |  |  |
| 212 | #2, 17 m @ 330, gas (top) | 145 | 10.747 | 252.59 | 1305.7 | 39.6 | 75.6 | 0.524 | 2.89e+07 | 93.0 | 21.081 | 0.22663 |
| 213 | #2, 17 m @ 330, gas grey (mid) | 140 | 13.307 | 292.75 | 1570.2 | 39.6 | 73.7 | 0.537 | 3.62e+07 | 134 | 32.206 | 0.24030 |
| 214 | #2, 17 m @ 330, gas grey (bot) | 140 | 12.536 | 344.15 | 1410.9 | 39.6 | 74.4 | 0.532 | 3.21e+07 | 108 | 25.479 | 0.23515 |
|  | AVERAGE: 212–214 |  |  |  |  |  |  |  |  | 112 |  |  |
| 215 | #2, 17 m @ 330, electric grey (top) | 112 | 14.005 | 442.60 | 1126.0 | 38.4 | 72.9 | 0.527 | 2.44e+07 | 63.0 | 14.468 | 0.22958 |
| 216 | #2, 17 m @ 330 electric grey (mid) | 108 | 13.320 | 440.58 | 997.98 | 38.4 | 63.8 | 0.602 | 2.65e+07 | 48.5 | 14.981 | 0.30862 |
| 217 | #2, 17 m @ 330, electric grey (bot) | 107 | 14.753 | 538.06 | 1040.5 | 38.4 | 68.2 | 0.563 | 2.50e+07 | 53.3 | 14.229 | 0.26700 |
|  | AVERAGE: 215–217 |  |  |  |  |  |  |  |  | 55.0 |  |  |
| 218 | #2, 17 m @ 360, gas grey (top) | 166 | 9.0216 | 140.32 | 1357.3 | 44.5 | 75.9 | 0.586 | 4.02e+07 | 140 | 40.926 | 0.29175 |
| 219 | #2, 17 m @ 360, gas grey (mid) | 155 | 9.9439 | 135.76 | 1405.5 | 44.5 | 77.5 | 0.574 | 4.04e+07 | 151 | 42.071 | 0.27880 |
| 220 | #2, 17 m @ 360, gas grey (bot) | 151 | 11.587 | 349.97 | 1399.7 | 44.5 | 77.5 | 0.574 | 4.02e+07 | 150 | 41.720 | 0.27880 |
|  | AVERAGE: 218–220 |  |  |  |  |  |  |  |  | 147 |  |  |
| 221 | #2, 17 m @ 360, electric grey (top) | 140 | 8.8571 | 209.47 | 1030.5 | 42.4 | 73.7 | 0.575 | 2.83e+07 | 70.1 | 19.640 | 0.27998 |
| 222 | #2, 17 m @ 360 electric grey (mid) | 130 | 11.257 | 329.61 | 1133.8 | 42.4 | 73.0 | 0.581 | 3.16e+07 | 84.8 | 24.240 | 0.28587 |
| 223 | #2, 17 m @ 360, electric grey (bot) | 145 | 8.0343 | 82.931 | 1082.0 | 42.4 | 74.2 | 0.571 | 2.94e+07 | 77.4 | 21.355 | 0.27586 |
|  | AVERAGE: 221–223 |  |  |  |  |  |  |  |  | 77.5 |  |  |
| 224 | #2, 17 m @ 390, gas grey (top) | 121 | 13.675 | 459.33 | 1195.3 | 39.6 | 70.5 | 0.562 | 2.95e+07 | 77.2 | 20.493 | 0.26558 |
| 225 | #2, 17 m @ 390, gas grey (mid) | 129 | 16.846 | 545.65 | 1627.5 | 39.6 | 68.7 | 0.576 | 4.18e+07 | 142 | 40.065 | 0.28117 |
| 226 | #2, 17 m @ 390, gas grey (bot) | 124 | 16.340 | 502.06 | 1524.1 | 39.6 | 73.0 | 0.542 | 3.57e+07 | 126 | 30.964 | 0.24558 |
|  | AVERAGE: 224–226 |  |  |  |  |  |  |  |  | 115 |  |  |
| 227 | #2, 17 m @ 390 electric grey (top) | 125 | 12.567 | 346.38 | 1224.5 | 43.4 | 72.7 | 0.597 | 3.64e+07 | 106 | 32.037 | 0.30329 |
| 228 | #2, 17 m @ 390 electric grey (mid) | 130 | 11.766 | 373.14 | 1156.4 | 43.4 | 74.5 | 0.583 | 3.31e+07 | 94.6 | 27.208 | 0.28773 |
| 229 | #2, 17 m @ 390, electric grey (bot) | 124 | 10.249 | 40.545 | 1230.3 | 43.4 | 73.3 | 0.592 | 3.61e+07 | 107 | 31.818 | 0.29800 |
|  | AVERAGE: 227–229 |  |  |  |  |  |  |  |  | 102 |  |  |
| 230 | #2, 30 m @ 390, gas grey (top) | 132 | 11.818 | 299.50 | 1260.5 | 42.4 | 72.0 | 0.589 | 3.58e+07 | 105 | 30.804 | 0.29454 |
| 231 | #2, 30 m @ 390, gas grey (mid) | 135 | 9.5945 | 149.91 | 1145.3 | 42.4 | 71.8 | 0.591 | 3.27e+07 | 86.3 | 25.576 | 0.29631 |
| 232 | #2,30 m @ 390, gas grey (bot) | 132 | 11.543 | 167.83 | 1355.8 | 42.4 | 74.3 | 0.571 | 3.67e+07 | 122 | 33.438 | 0.27504 |
|  | AVERAGE: 230–232 |  |  |  |  |  |  |  |  | 104 |  |  |
| 233 | #2, 30 m @ 390, electric grey (top) | 147 | 6.8642 | 104.22 | 904.82 | 44.7 | 76.1 | 0.587 | 2.70e+07 | 63.2 | 18.504 | 0.29292 |
| 234 | #2, 30 m @ 390 electric grey (mid) | 157 | 6.5732 | 118.71 | 913.28 | 44.7 | 77.5 | 0.577 | 2.65e+07 | 64.5 | 18.169 | 0.28155 |
| 235 | #2, 30 m @ 390, electric grey (bot) | 146 | 8.8149 | 140.57 | 1146.4 | 44.7 | 75.4 | 0.593 | 3.47e+07 | 101 | 30.259 | 0.29881 |

TABLE 7-continued

| Example | Sample | C.E. | Slope | Intercept | 1/Rc | Thick | Radius | h/b | Pressure q | G | q2b/E | f (h/b) |
|---|---|---|---|---|---|---|---|---|---|---|---|---|
| | AVERAGE: 233–235 | | | | | | | | | 76.3 | | |

TABLE 8

| Example | Sample | C.E. | Slope | Intercept | 1/Rc | Thick | Radius | h/b | Pressure q | G | q2b/E | f (h/b) |
|---|---|---|---|---|---|---|---|---|---|---|---|---|
| 236 | TPO control #1 | 75.0 | | | 136.00 | 59 | 99.0 | 0.596 | 5.48e+06 | 3.27 | 0.98954 | 0.30219 |
| 237 | TPO 600 grit | 96.0 | | | 186.00 | 88 | 97.0 | 0.907 | 1.94e+07 | 19.0 | 12.193 | 0.64128 |
| 238 | TPO 400 grit | 90.0 | | | 199.00 | 75 | 95.0 | 0.789 | 1.50e+07 | 13.8 | 7.1347 | 0.51716 |
| 239 | TPO control #2 | 60.0 | | | 79.000 | 55 | 78.0 | 0.705 | 3.77e+06 | 0.873 | 0.36954 | 0.42343 |
| 240 | TPO sand blast | 88.0 | | | 72.000 | 81.25 | 94.0 | 0.864 | 6.57e+06 | 2.26 | 1.3511 | 0.59733 |

COMPUTER PROGRAM LISTING

```
frmLIDSi - 1
    Dim xsig(15000), ysig(15000)
    Dim ymin!, ymax!, d%, zz!, sc%, axis2%
Private Sub cmdAnalyze_Click ( )
    Call analyze1
End Sub
Private Sub cmdExit_Click ( )
    Unload Me
    End
End Sub
Private Sub cmdget_file_Click ( )
    Call get_file1
    Call analyze1
End Sub
Private Sub cmdgetdata_Click ( )
    Call Lecroy_init
    Call getdata1
    Call analyze1
    Call Lecroy_init
End Sub
Private Sub cmdlecroyinit_Click ( )
    Call Lecroy_init
End Sub
Private Sub cmdinitlecroy_Click ( )
    Call Lecroy_init
End Sub
Privatge Sub cmdmove_dcs_Click ( )
    Call dcs_move
End Sub
Private Sub cmdOrigin_Click ( )
    Call dcs_origin
End Sub
Private Sub get_file1 ( )
    a$ = txtFilename.Text
    d% = 1000
    ymin = 0: ymax = 0
    Open a$ For Input As #3
frmLIDSi - 2
    for j = 1 To d%
        Input #3, xsig(j), ysig(j)
        If ysig(j) > ymax Then ymax = ysig(j)
        If ysig(j) < ymin Then min = ysig(j)
    Next j
    Close #3
    Call plotdata
End Sub
Public Sub analyze1 ( )
'calculate the curvature of the data set
'first calculate average of presignal baseline
    Radcurve = 0
    baseline = 0
    For j = 1 To 90
        baseline = baseline + ysig(j)
    Next j
    m1 = baseline / 90
'input zero HeNe baseline and other parameters
    m2 = Val (txtzeroHeNe.Text)   'zero HeNe signal
```

COMPUTER PROGRAM LISTING

```
    m3 = 0.04              'initial HeNe sport size (cm)
    m4 = 0.00006328        'HeNe wavelength (cm)
    m5 = 79.433            'HeNe beam parameter
    m6 = 43.4              'distance from HeNe to lens
    m7 = 9.8               'distance from lens to sample
    m8 = 9.75              'focal length of lens
    m9 = 25.9              'distance from sample to aperture
    pi = 3.14159
    ap = Val(txtaprad.Text)      'radius of aperture
(m10 = 4 * m9 ^ 2 * (-(m6 ^ 2 + m5 ^ 2) * (-m7 + m8) ^ 2 + 2 * m8 * m6 * (-m7 + m8) * m7 - m8 ^
2 * m7 ^ 2)
(m11 = 4 * ((m6 ^2 + m9 * m6 +^ m5 ^ 2) * (m8 - m7) ^ 2 - m9 * m8 ^ 2 * m6 + (m8 - m7) * (m9 *
m6 ^ 2 + m9 * m5 ^ 2 - 2 * m8 * m6 * m7) + m8 ^ 2 * m7 ^ 2 + m9 * m8 * m7 ^ 2) * m9
'calculate average y signal
total_1 = 0
For j = 300 To 400
    total_1 = total_1 + ysig(j)
Next j
total_1 = total_1 / 101
'calculate curvature
temp0 = Sqr (-2 * ap 2 / (Log(1 - (total_1 - m2) / (m1 - m2))))
temp1 = M4 * (2 * (m7 - m8) * (-m8 * m6 * m7 + m9 * m6 2 + m9 * m5 2) - (m6 2 + m5 2)
(-m7 + m8) ^ 2 - m9 ^ 2 * (-m7 + m6) ^ 2 - m7 ^ 2 * m7 ^ 2 - 2 * m9 * m8 * m7 ^ 2 - 2 * m9 * m8
* m7 ^ 2 + 4 * m9 * m8 * m6 * m7 - m9 ^ 2 * m5 ^ 2) + temp0 ^ 2 * m5 * pi * m7 ^ 2) / m4
temp2 = -0.5 * (-Sqr(m11 ^ 2 - 4 * temp1 * m10) + m11) / temp1
Radcurve = 100 / temp2
txtresult.Text = "1/Rc = " & Radcurve
End Sub
Public Sub getdata1 ( )
    b$ = Space$ (5): c$ = Space$ (2): g$ = Space$ (20)
frmLIDSi - 3
    picdiag.Cls
    txtfilesaved.Text = " "
    'find out the channel-1 volts/div
    a$ = "c1vd ?"
    Call ibwrt (sc%, a$)
    Call ibrd (sc%, g$)
    w = Val(Mid$(g$, 6, 9))
    picdiag.Print "The channel 1 volts/div scale = ", w
    'find out the time/div
    a$ = "td ?"
    Call ibwrt (sc%, a$)
    Call ibrd (sc%, g$)
    z = Val (Mid$(g$, 4, 8))    'z is time/div
    picdaig.Print "The time/div scale = ", z
    zz = z * 10                 'zz is total scan time
    z = zz / 1000               'z is now time/point
    'note that the number in the denom. times the number in a$ is the total number of points in
the scope's file
    picdiag.Print "Now reading memory D baseline"
    a$ = "rd,md.da,2;": Call ibwrt (sc%, a$)
    Call ibrd(sc%, c$): picdiag.Print "This should be #L:", c$
    Call ibrd(sc%, b$): d% = Int(Val(b$))
    picdiag.Print "The number of points to tranfer = ", d%
    total = 0
    For j = 1 To d%
    Call ibrd(sc%, b$)
    temp = (Val(b$) - 32640) * w / 8160
    total = total + temp
    'If (Int(j / 100)) * 100 - j = 0 Then
    '       picdiag.Print j, tep
    'End If
    Next j
    total = total / d%
    picdiag.Print "The average of the baseline scan = ", total
    frmLIDS1.txtzeroHeNe.Text = total
    picdiag.Print "Now reading memory C signal"
    a$ = "rd,mc.da,2;": Call ibwrt(sc%, a$)
    Call ibrd(sc%, c$): picdiag.Print "This should be #L:", c$
    Call ibrd(sc%, b$): d% = Int(Val(b$))
    picdiag.Print "The number of points to transfer = ", d%
    ymax = 0: ymin = 0
    For j = 1 To d%
        Call ibrd(sc%, b$)
        xsig(j) = j * z
        ysig(j) = (Val(b$) - 32640) * w / 8160
        'If (Int(j / 500)) * 500 - j = 0 Then
    '       picdiag.Print xsig(j), ysig(j)
```

-continued

COMPUTER PROGRAM LISTING

```
        'End If
        If ysig(j) > ymax Then umax = ysig(j)
        If ysig(j) < ymin Then ymin = ysig(j)
    Next j
    Call plotdata
    Call ibloc(sc%)
    Call ibloc(sc%)
End Sub
Public Sub Lecroy_init( )
a$ = "gpib0": Call ibfind (a$, bd%)
Call ibsic(bd%)
a$ = "Lecroy"
frmLIDSi - 4
    Call ibfind(a$, sc%)
    Call ibclr(sc%)
    a$ = "cfmt,1,word,ufix;"
    Call ibwrt(sc%, a$)
    Call iblock(sc%)
End Sub
Private Sub cmdsentolecroy_Click ( )
    Call Lecroy_init
    a$ = txttoLecroy.TGext
    Call ibwrt(sc%, a$)
End Sub
Public Sub dcs_origin( )
    a$ = "gpib0": Call ibfind(a$, bd%)
    Call isic(bd%)
    a$ = "axis2"
    Call ibfind(a$, f%)
    b$ = "pa0"
    Call ibwrt(f%, b$)
End Sub
Public Sub dcs_move ( )
    a$ = "gpib0": Call ibfind(a$, bd%)
    Call ibsic(bd%)
    a$ = "axis2"
    Call ibfind(a$, f%)
    b$ = "va500"
    Call ibwrt(F%, b$)
    b$ = "kp1500"
    Call ibwrt(f%, b$)
    b$ = "kd10000"
    Call ibwrt(f%, b$)
    b$ = "ki200"
    Call ibwrt(f%, b$)
    b$ = "il200"
    Call ibwrt(f%, b$)
    b$ = "ds0"
    Call ibwrt(f%, b$)
    b$ = "uf"
    Call ibwrt(f%, b$)
    b$ = txtdcs_command.Text
    Call ibwrt(f%, b$)
End Sub
Private Sub Text1_Change ( )
End Sub
Private Sub Command1_Click ( )
    Call savedata
End Sub
Private Sub cmdsavedata_Click ( )
    Call savedata
frmLIDSi - 5
End Sub
Private Sub Label1_Click ( )
End Sub
Public Sub savedata ( )
    d_name = txtdataname.Text & txtfilename2.Text & ".prn"
    Open d_name$ For Output As #2
    For j = 1 To d%
        Write #2, xsig(j), ysig(j)
    Next j
    Close #2
    txtfilesaved.Text = "FIle Saved!"
End Sub
Public Sub plotdata( )
    picMyplot.Cls
    picMyplot.Scale (0, ymax & 1.1)-(d%, ymin * 1.1)
    picMyplot.PSet (1, ysig(1))
```

| COMPUTER PROGRAM LISTING -continued |
| --- |
| For j = 2 To d% |
|     picMyplot.Line –(j, ysig(j)) |
| Next j |
| End Sub |

What is claimed is:

1. A process for determining adhesion of a film system, comprising the steps of: (a) applying a pulse of electromagnetic radiation to a film system, said pulse having sufficient intensity to ablate a portion of the film system under adiabatic conditions; (b) forming a blister in the film system with the electromagnetic radiation; (c) determining a critical pulse energy occurring when the blister is strained to the point where an interfacial crack just begins to form; (d) determining the curvature of the blister at the critical pulse energy; (e) determining a critical internal pressure of the blister at the critical pulse energy; and (f) relating the critical internal pressure of the blister to an adhesion parameter to determine the adhesion of the film system.

2. The process of claim 1 wherein the film system comprises a substrate and at least one transparent coat.

3. The process of claim 2 wherein the film system further comprises at least one opaque coat.

4. The process of claim 3 wherein the film system comprises the substrate, at least one opaque coat applied to a top surface of the substrate and one transparent coat applied to a top surface of a last applied opaque coat and the blister forms at an interface between the transparent coat and the last applied opaque coat.

5. The process of claim 3 wherein the opaque coat is a primer and the transparent coat is an unpigmented basecoat.

6. The process of claim 3 wherein the opaque coat is a basecoat and the transparent coat is a clear topcoat.

7. The process of claim 2 wherein the substrate is selected from the group consisting of: metal, polymer and ceramic.

8. The process of claim 4 wherein the substrate is a metal, the opaque coat is an electrocoat applied to the top surface of the substrate, and the transparent coat is a primer applied to the top surface of the electrocoat.

9. The process of claim 1 wherein the critical pulse energy is determined by exposing the film system to a range of pulse energies and inspecting the blisters to determine at which pulse energy the blister begins to crack.

10. The process of claim 1 wherein the initial curvature of the blister at the critical pulse energy is determined by measuring an initial radius of curvature of a plurality of blisters formed at various pulse energies, inverting these measured values for the initial radius of curvature, plotting the inverted values against the varied pulse energies, fitting this plot to a straight line, and extrapolating the value for the initial curvature of the blister from this linear plot to the previously determined critical pulse energy.

11. The process of claim 10 wherein the initial radius of curvature measured value is made by reflecting a laser beam off the top surface of the blister, measuring the transmitted intensity of the beam through an aperture, determining the measured value of the beam spot size, and relating the measured value of the beam spot size to the initial radius of curvature.

12. The process of claim 1 wherein the critical internal pressure of the blister at the critical pulse energy is determined by relating variables comprising the flexural rigidity of the transparent topcoat, the modulus of the transparent topcoat, Poisson's ratio of the transparent topcoat, the thickness of the transparent topcoat, the radius of the blister, the initial radius of curvature of the blister and constants based on a boundary condition selected for the film system.

13. The process of claim 1 wherein the adhesion parameter is determined by relating the critical internal pressure of the blister at the critical pulse energy to a total strain energy in the film system at the critical pulse energy.

14. The process of claim 1 further comprising the steps of:

comparing the adhesion parameter of one film system with the adhesion parameter of a second film system which differs from the first film system in a variable to identify the film system possessing a higher value for the adhesion parameter; and adjusting the preparation of a third film system to incorporate or substitute for another variable, the variable of the first or second film system possessing the higher value for the adhesion parameter to improve the adhesion of the third film system.

* * * * *